(12) United States Patent
Yano et al.

(10) Patent No.: US 8,188,297 B2
(45) Date of Patent: May 29, 2012

(54) INDOLIUM COMPOUND AND OPTICAL RECORDING MATERIAL

(75) Inventors: Toru Yano, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 897 days.

(21) Appl. No.: 12/295,432

(22) PCT Filed: Mar. 23, 2007

(86) PCT No.: PCT/JP2007/055999
§ 371 (c)(1),
(2), (4) Date: Sep. 30, 2008

(87) PCT Pub. No.: WO2007/114074
PCT Pub. Date: Oct. 11, 2007

(65) Prior Publication Data
US 2009/0296554 A1    Dec. 3, 2009

(30) Foreign Application Priority Data
Mar. 31, 2006    (JP) .................................. 2006-096535

(51) Int. Cl.
*C07D 209/02*    (2006.01)
*G11B 11/12*    (2006.01)
(52) U.S. Cl. ..................................... 548/402; 369/13.56
(58) Field of Classification Search ............ 548/402
See application file for complete search history.

(56) References Cited

U.S. PATENT DOCUMENTS

| 7,014,981 B2 | 3/2006 | Wang et al. |
| 2002/0001774 A1 | 1/2002 | Je et al. |
| 2002/0028918 A1 | 3/2002 | Kasada et al. |
| 2003/0202458 A1 | 10/2003 | Wang et al. |
| 2006/0237915 A1 | 10/2006 | Kita et al. |

FOREIGN PATENT DOCUMENTS

| EP | 1 130 063 | 9/2001 |
| JP | 11-34489 | 2/1999 |
| JP | 11-170695 | 6/1999 |
| JP | 2001-342366 | 12/2001 |
| JP | 2002-206061 | 7/2002 |
| JP | 2003-171571 | 6/2003 |
| JP | 2009-231359 | 8/2003 |
| JP | 2003-313447 | 11/2003 |
| JP | 2003-321450 | 11/2003 |
| JP | 2004-195765 | 7/2004 |
| JP | 2006-312710 | 11/2006 |
| WO | 2006/011306 | 2/2006 |
| WO | 2006/018352 | 2/2006 |
| WO | 2006/035554 | 4/2006 |
| WO | 2006/038464 | 4/2006 |
| WO | 2006/046374 | 5/2006 |

OTHER PUBLICATIONS

European Patent Office issued an European Search Report dated Jun. 30, 2010, Application No. 07739440.1.

*Primary Examiner* — Shawquia Young
(74) *Attorney, Agent, or Firm* — Young & Thompson

(57) ABSTRACT

An indolium compound is represented by formula (I):

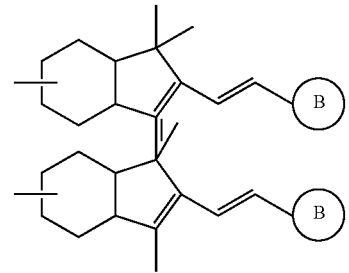

Ring A: a benzene or naphthalene ring. Ring B: 5- or 6-membered heterocyclic or aromatic ring. Z: alkyl group having 1-8 carbon atoms, may be substituted with a halogen atom or interrupted by —O—, —CO—, —OCO—, or —COO—, a sulfonyl group having a hydrocarbyl group having -8 carbon atoms, a sulfinyl group having a hydrocarbyl group having 1-8 carbon atoms, an alkylamino group having an alkyl group having 1-8 carbon atoms, a dialkylamino group having alkyl groups having 1-8 carbon atoms, a cyano group, a nitro group, a hydroxyl group, or a halogen group. $R^1$: group represented by formula (II) or (II'). $R^2$: organic group having 1-30 carbon atoms or group represented by formula (II), (II'), or (III). Y: group represented by formula (III). n: integer 0-4; $An^{m-}$: m-valent anion, m is 1 or 2. p: coefficient for neutral charge.

11 Claims, 2 Drawing Sheets

[Fig. 1]
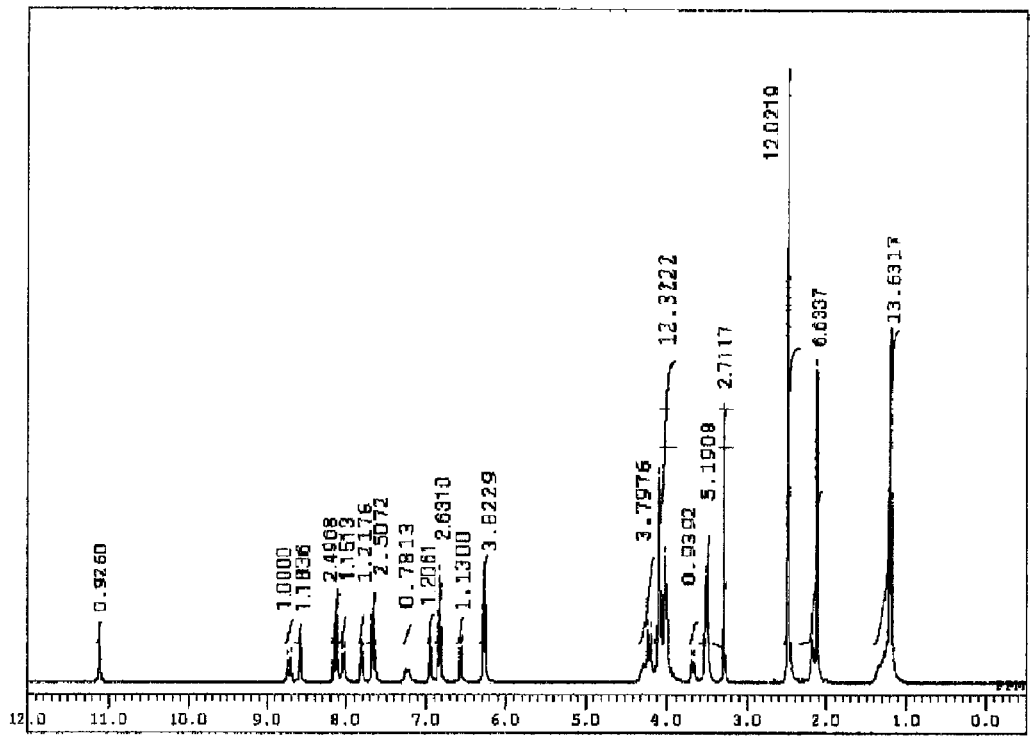
[Fig. 2]
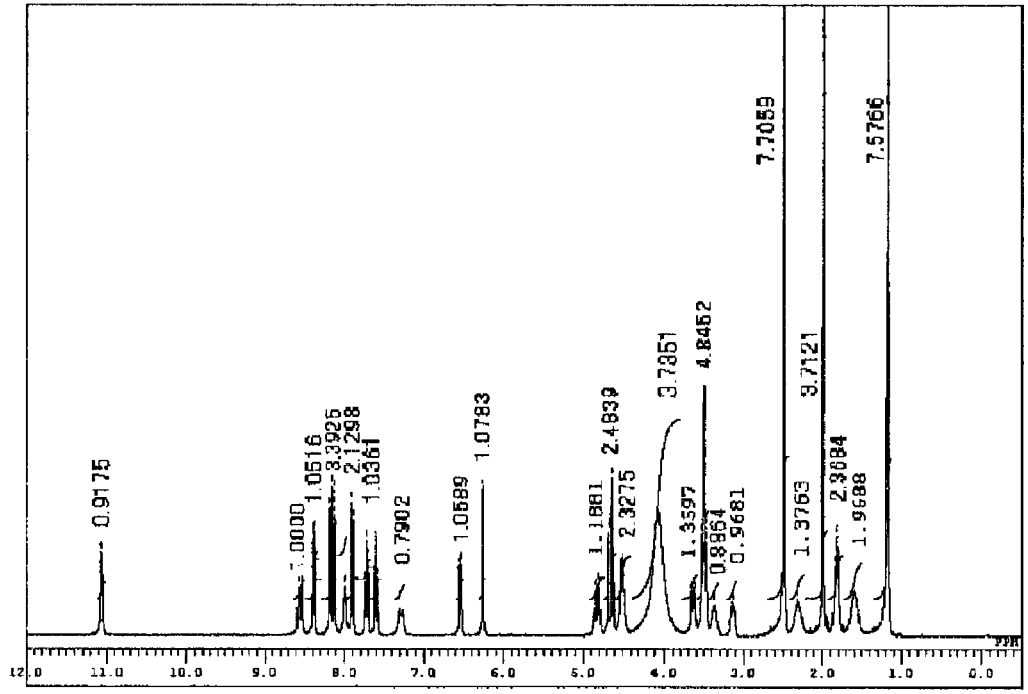

[Fig. 3]
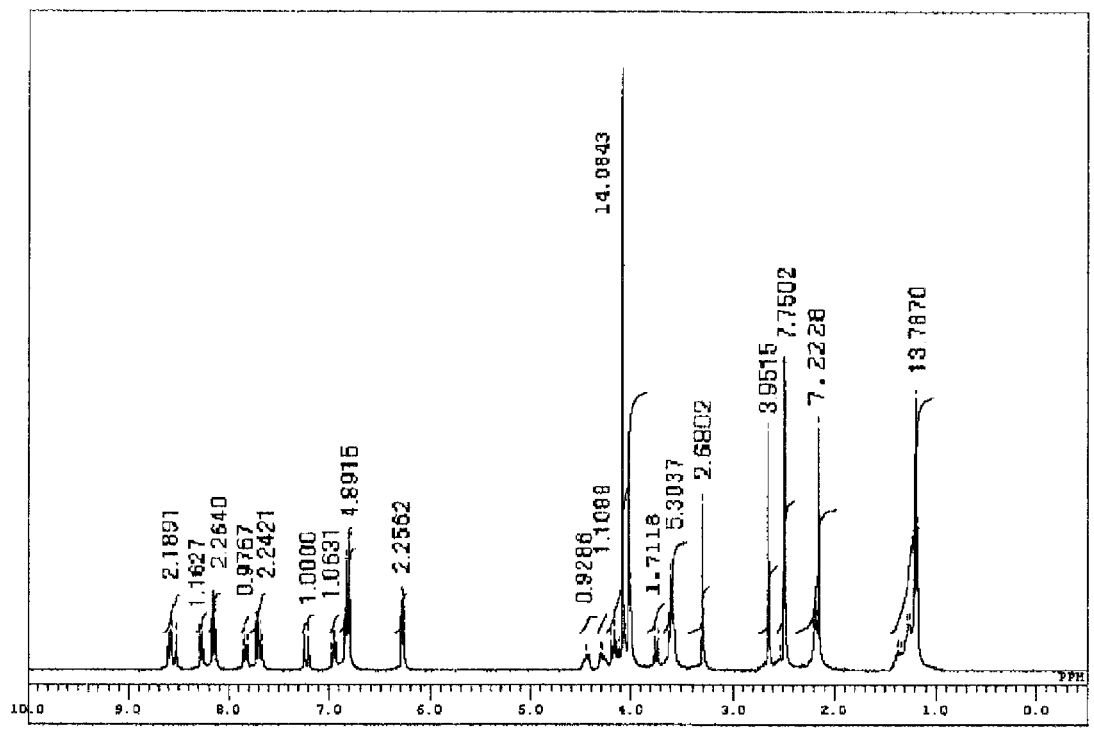

INDOLIUM COMPOUND AND OPTICAL RECORDING MATERIAL

TECHNICAL FIELD

The present invention relates to a novel indolium compound which is used mainly for an optical recording material and the like, and also relates to an optical recording material comprising the indolium compound. Particularly, the present invention relates to an optical recording material used for an optical recording medium, information being recorded thereon as information patterns by means of a laser and the like. More particularly, the present invention relates to an optical recording material used for an optical recording medium which is capable of high-density optical recording and reproduction by a laser and the like, the laser having emissions in ultraviolet and visible regions, and being of low energy.

BACKGROUND ART

The optical recording media are in widespread use, generally due to its superior characteristics such as large recording capacities, noncontact recording or reproduction, and the like. In the write-once optical discs such as WORM, CD-R, DVD±R, and the like, recording is carried out by focusing the laser light on a minute area of the recording layer to change properties of the optical recording layer, while reproduction is performed based on a difference in intensities of light reflected from the recorded area and non-recorded area.

Compounds having a strong absorption between 550 nm and 620 nm, especially those having absorption maxima (λmax) between 550 and 620 nm are being used as optical recording materials to form optical recording layers of optical recording media such as DVD-R and the like.

As the optical recording material described above, there are many reports on indolium compounds containing an indole ring, which has a merit that it can correspond to high-speed recording due to its high sensitivity. For example, Patent Document Nos. 1 to 6 report styrylindolium compounds. Also, Patent Document 7 reports a cyanine compound of a low decomposition temperature, which has a benzyl group introduced at the 3-position of the indole ring. It is thought that a compound which decomposes at a low temperature forms a recorded portion (pit) of an optical recording layer easily and is considered to adapt to a high-speed recording medium.

However, these materials have not shown satisfactory performance in terms of light stability and recording characteristics.

Patent Document No. 1: Japanese Patent Laid-Open Publication No. H11-34489
Patent Document No. 2: Japanese Patent Laid-Open Publication No. H11-170695
Patent Document No. 3: Japanese Patent Laid-Open Publication No. 2001-342366
Patent Document No. 4: Japanese Patent Laid-Open Publication No. 2002-206061
Patent Document No. 5: Japanese Patent Laid-Open Publication No. 2003-313447
Patent Document No. 6: Japanese Patent Laid-Open Publication No. 2003-321450
Patent Document No. 7: Japanese Patent Laid-Open Publication No. 2003-231359

DISCLOSURE OF THE INVENTION

Problems to be Solved by the Invention

Accordingly, an object of the present invention is to provide a novel indolium compound which has high light resistance and shows thermal decomposition behavior suitable for an application in high-speed optical recording, and to provide an optical recording material comprising the indolium compound.

Means for Solving the Problems

The present inventors conducted diligent research and, as a result, found a novel indolium compound of a specific cationic structure which shows excellent thermal decomposition behavior as an optical recording material. This finding led to the present invention.

The present invention has accomplished the object by providing an indolium compound represented by the following general formula (I).

[Formula 1]

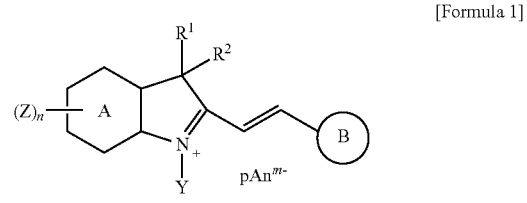

wherein the ring A represents a benzene or naphthalene ring; the ring B represents a 5- or 6-membered heterocyclic or an aromatic ring; Z represents an alkyl group having 1 to 8 carbon atoms which may be substituted with a halogen atom or may be interrupted by —O—, —CO—, —OCO—, or —COO—, a sulfonyl group having a hydrocarbyl group having 1 to 8 carbon atoms, a sulfinyl group having a hydrocarbyl group having 1 to 8 carbon atoms, an alkylamino group having an alkyl group having 1 to 8 carbon atoms, a dialkylamno group having alkyl groups having 1 to 8 carbon atoms, a cyano group, a nitro group, a hydroxyl group, or a halogen group; $R^1$ represents a group represented by the following general formula (II) or (II'); $R^2$ represents an organic group having 1 to 30 carbon atoms or a group represented by the following general formula (II), (II'), or (III); Y represents a group represented by the general formula (III); n represents an integer from 0 to 4; $An^{m-}$ represents an m-valent anion, where m is 1 or 2; p represents a coefficient to keep the charge neutral:

[Formula 2]

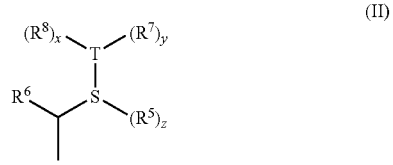

(II)

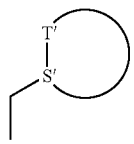
(II')

in the general formula (II), the bond between S and T is a double or triple bond; S represents a carbon atom; T represents a carbon, oxygen, or nitrogen atom; x, y, and z represent 0 or 1; $R^5$ represents a hydrogen atom, a halogen atom, an alkyl group having 1 to 4 carbon atoms which may be substituted with a halogen atom, or an alkoxy group having 1 to 4 carbon atoms which may be substituted with a halogen atom; $R^6$, $R^7$, and $R^8$ each independently represent a hydrogen atom, a halogen atom, an alkyl group having 1 to 4 carbon atoms which may be substituted with a halogen atom; $R^6$ and $R^8$ may be linked together to form a ring structure; in the general formula (II'), the bond between S' and T' is a double bond; S' represents a carbon atom; T' represents a carbon, oxygen, or nitrogen atom; the ring containing S' and T' represents a 5-membered ring which may contain a hetero atom or a 6-membered ring which may contain a hetero atom, or a naphthalene, quinoline, isoquinoline, anthracene, or anthraquinone ring; these rings containing S' and T' may be substituted with a halogen atom, or a nitro, cyano, alkyl, or alkoxy group:

[Formula 3]

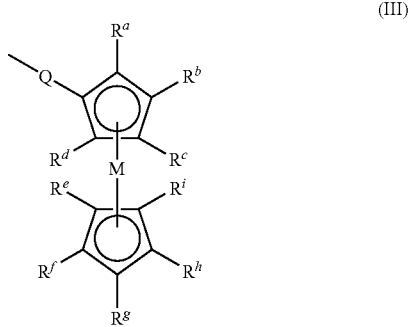
(III)

wherein $R^a$ to $R^i$ each independently represent a hydrogen atom or an alkyl group having 1 to 4 carbon atoms, where the methylene group of the alkyl group may be replaced by —O— or —CO—; Q represents a direct bond or an alkylene group having 1 to 8 carbon atoms which may be substituted, where the methylene group of the alkylene group may be replaced by —O—, —S—, —CO—, —COO—, —OCO—, —SO$_2$—, —NH—, —CONH—, —NHCO—, —N═CH—, or —CH═CH—; M represents Fe, Co, Ni, Ti, Cu, Zn, Zr, Cr, Mo, Os, Mn, Ru, Sn, Pd, Rh, Pt, or Ir.

In addition, the present invention has accomplished the object by providing an optical recording material comprising at least one kind of the indolium compound, the optical recording material being used to form an optical recording layer of an optical recording medium which has an optical recording layer disposed on a substrate.

Further, the present invention has accomplished the object by providing an optical recording medium comprising an optical recording layer disposed on a substrate, the recording layer comprising the optical recording material.

BRIEF DESCRIPTION OF THE DRAWINGS

FIG. 1 shows a $^1$H-NMR spectrum of a hexafluorophosphate salt of Compound No. 1

FIG. 2 shows a $^1$H-NMR spectrum of a perchlorate salt of Compound No. 2.

FIG. 3 shows a $^1$H-NMR spectrum of a hexafluorophosphate salt of Compound No. 3.

BEST MODE FOR CARRYING OUT THE INVENTION

Hereafter, the indolium compound of the present invention and the optical recording material comprising the indolium compound will be described in detail based on preferable embodiments.

First, the indolium compound represented by the general formula (I) will be described.

In the general formula (I), the alkyl group having 1 to 8 carbon atoms, represented by Z which is a substituent of the benzene or naphthalene ring represented by the ring A, may be substituted with a halogen group or interrupted by —O—, —CO—, —OCO—, or —COO—, the point of substitution by the halogen group and the point of interruption by —O—, —CO—, —OCO—, or —COO— being optional, including a case where —O—, —CO—, —OCO—, or —COO— is linked directly to the ring A. The alkyl group having 1 to 8 carbon atoms includes methyl, ethyl, propyl, isopropyl, butyl, sec-butyl, tert-butyl, isobutyl, amyl, isoamyl, tert-amyl, hexyl, cyclohexyl, heptyl, isoheptyl, tert-heptyl, n-octyl, isooctyl, tert-octyl, 2-ethylhexyl, chloromethyl, dichloromethyl, trichloromethyl, trifluoromethyl, pentafluoroethyl, methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, chloromethyloxy, dichloromethyloxy, trichloromethyloxy, trifluoromethyloxy, pentafluoroethyloxy, 2-hydroxyethyloxy, 2-methyl-2-hydroxyethyloxy, 1-methyl-2-hydroxyethyloxy, 3-hydroxypropyloxy, 2-(2-hydroxyethoxy)ethyloxy, 2-methoxyethyloxy, 2-butoxyethyloxy, 2-methyl-2-methoxyethyloxy, 1-methyl-2-methoxyethyloxy, 3-methoxypropyloxy, 2-(2-methoxyethoxy)ethyloxy, acetyl, acetonyl, butan-2-on-1-yl, butan-3-on-1-yl, cyclohexan-4-on-1-yl, trichloroacetyl, trifluoroacetyl, acetoxy, ethanecarbonyloxy, propanecarbonyloxy, butanecarbonyloxy, trifluororacetoxy, and the like. In addition, the hydrocarbyl group having 1 to 8 carbon atoms, possessed by the sulfonyl or sulfinyl group which is represented by Z, includes an alkyl group such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, and the like; an alkenyl group such as vinyl, 1-methylethen-1-yl, propen-1-yl, propen-2-yl, propen-3-yl, butene-1-yl, buten-2-yl, 2-methylpropen-3-yl, 1,1-dimethylethen-2-yl, 1,1-dimethylpropen-3-yl, and the like; an aryl group such as phenyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, and the like; an arylalkyl group such as benzyl, 2-methylbenzyl, 3-methylbenzyl, 4-methylbenzyl, phenethyl, 2-phenylpropan-2-yl, styryl, and the like. As the alkyl group having 1 to 8 carbon atoms, possessed by the alkylamino or dialkylamide group which is represented by Z, includes the same alkyl groups exemplified above; a halogen group represented by Z includes fluorine, chlorine, bromine, iodine, and the like.

There is no particular restriction on the organic group having 1 to 30 carbon atoms and represented by $R^2$, the organic group including, for example, an alkyl group such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, octadecyl, and the like; an alkenyl group such as vinyl, 1-methylethenyl, 2-methylethenyl, propenyl, butenyl, isobutenyl, pentenyl, hexenyl, heptenyl, octenyl, decenyl, pentadecenyl, 1-phenylpropen-3-yl, and the like; an alkylaryl group such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, cyclohexylphenyl, and the like; an arylalkyl group such as benzyl, phenethyl, 2-phenylpropan-2-yl, diphenylmethyl, triphenylmethyl, styryl, cinnamyl, and the like; groups wherein these hydrocarbyl groups are interrupted by an ether bond or a thioether bond such as, for example, 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, 2-phenylthioethyl, and the like. Further, these groups may be substituted by the following substituents.

The substituents include an alkyl group such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, decyl, and the like; an alkoxy group such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, decyloxy, and the like; an alkylthio group such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, 2-ethylhexylthio, and the like; an alkenyl group such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicocenyl, tricocenyl, and the like; an arylalkyl group such as benzyl, phenethyl, diphenylmethyl, triphenylmethyl, styryl, cinnamyl, and the like; an aryl group such as phenyl, naphthyl, and the like; an aryloxy group such as phenoxy, naphthyloxy, and the like; an arylthio group such as phenylthio, naphthylthio, and the like; a heterocyclic group such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, 2,4-dioxyoxazolidin-3-yl, and the like; a halogen atom such as fluorine, chlorine, bromine, iodine, and the like; an acyl group such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, tert-butoxycarbonyl, n-octadecyloxycarbonyl, carbamoyl, and the like; an acyloxy group such as acetyloxy, benzoyloxy, and the like; a substituted amino group such as amino, ethylamino, dimethylamino, diethylamino, butylamino, cyclopentylamino, 2-ethylhexylamino, dodecylamino, anilino, chlorophenylamino, toluidino, anicidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, tert-butoxycarbonylamino, n-octadecyloxycarbonylamino, N-methylmethoxycarbonylamino, phenoxycarbonylamino, sulfamoylamino, N,N-dimethylaminosulfonylamino, methylsulfonylamino, butylsulfonylamino, phenylsulfonylamino, and the like; a sulfonamide, sulfonyl, carboxyl, cyano, sulfo, hydroxy, nitro, mercapto, imide, carbamoyl, sulfonamide groups, and the like. These groups may be further substituted. In addition, the carboxyl and sulfo groups may be in the form of salts.

In the general formula (I), the 5-membered heterocyclic ring represented by the ring B includes a pyrrole, furan, thiophene, pyrazolidine, pyrazole, imidazole, imidazolidine, oxazole, isoxazole, isoxazolidine, thiazole, isothiazolidine rings, and the like; the 6-membered ring represented by the ring B includes a piperazine, morpholine, thiomorpholine, urolidine, pyridine, pyrazine, pyrimidine, pyridazine, triazine rings, and the like. The 5- or 6-membered ring represented by the ring B may be condensed with other rings or may be substituted, with examples including a quinoline, isoquinoline, indole, urolidine, benzothiophene, benzoxazole, benzotriazole, azulene, phthalimide rings, and the like.

In the general formula (I), the anion represented by $An^{m-}$ includes as a monovalent anion, a halide ion such as a chloride, bromide, iodide, fluoride ions, and the like; an inorganic anion such as a perchlorate, chlorate, thiocyanate, hexafluorophosphate, hexafluoroantimonate, tetrafluoroborate ions, and the like; an organic sulfonate ion such as a benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate, and sulfonate ions described in Japanese Patent Laid-Open Publication No. 2004-53799, and the like; an organic phosphate-related ions such as an octyl phosphate, dodecyl phosphate, octadecyl phosphate, phenyl phosphate, nonylphenyl phosphate, 2,2'-methylenebis(4,6-di-tert-butylphenyl) phosphonate ions, and the like; a bistrifluoromethylsulfonylimide anion; a bisperfluorobutanesulfonylimide anion; a perfluoro-4-ethylcyclohexanesulfonate ion; a tetrakis(pentafluorophenyl)borate ion; and the like. As a divalent anion, a benzenedisulfonate, naphthalenedisulfonate ions, and the like may be cited. There may also be used, according to necessity, a quencher anion which can deactivate (quench) the active molecules in the exited state and anions of metallocene compounds such as ferrocene, ruthenocene, and the like which have an anionizable group such as a carboxylic acid, phosphonic acid, and sulfonic acid groups on the cyclopentadienyl group.

The quencher anion includes those represented by the following general formula (A) or (B), or formula (C) or (D), or anions described in Japanese Patent Laid-Open Publication Nos. S60-234892, H5-43814, H5-305770, H6-239028, H9-309886, H9-323478, H10-45767, H11-208118, 2000-168237, 2002-201373, 2002-206061, and 2005-297407;

Japanese Patent Application Publication No. H7-96334; International Publication No. WO/98/29257, and the like:

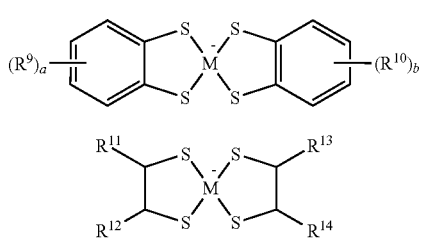

wherein M is the same as in the general formula (III); $R^9$ and $R^{10}$ each independently represent a halogen atom, an alkyl group having 1 to 8 carbon atoms, an aryl group having 6 to 30 carbon atoms, or a —$SO_2$-G group, G representing an alkyl, aryl that may be substituted with a halogen atom, dialkylamino, diarylamino, piperidino, or morpholino groups; a and b each independently represent a number from 0 to 4; further, $R^{11}$, $R^{12}$, $R^{13}$, and $R^{14}$ each independently represent an alkyl, alkylphenyl, alkoxyphenyl, or halogenated phenyl groups.

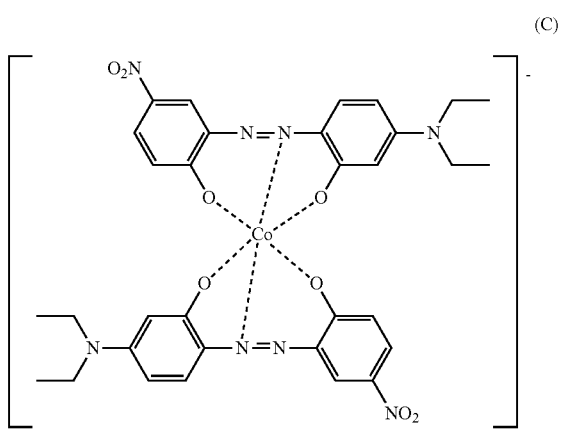

In the general formula (II), the alkyl group having 1 to 4 carbon atoms, represented by $R^5$ to $R^8$, includes methyl, ethyl, propyl, isopropyl, butyl, sec-butyl, tert-butyl, isobutyl, and the like; the alkoxy group having 1 to 4 carbon atoms, represented by $R^5$, includes methyloxy, chloromethyloxy, trifluoromethyloxy, cyanomethyloxy, ethyloxy, dichloroethyloxy, propyloxy, isopropyloxy, butyloxy, sec-butyloxy, tert-butyloxy, isobutyloxy, and the like.

In the general formula (II), the halogen atom represented by $R^5$ to $R^8$ includes fluorine, chlorine, bromine, and iodine. And the ring structure formed by linking of $R^6$ and $R^8$ includes a cyclopropane, cyclobutane, cyclopentane, cyclohexane, tetrahydropyran, piperidine, piperazine, pyrrolidine, morpholin, thiomorpholin, pyridine, pyrazine, pyrimidine, pyridazine, triazine, quinoline, isoquinoline, imidazole, oxazole, imidazolidine, pyrazolidine, isoxazolidine, isothiazolidine rings, and the like, where these rings may be condensed with other rings or may be substituted.

In the general formula (II'), the 5-membered ring which may contain an heteroatom includes a cyclopentene, cyclopentadiene, imidazole, thiazole, pyrrazole, oxazole, isoxazole, thiophene, furan, pyrrole rings, and the like; the 6-membered ring which may contain a heteroatom includes a benzene, pyridine, piperazine, piperidine, morpholin, pyrazine, pyrone, pyrrolidine rings, and the like.

In the general formula (III), the alkyl group having 1 to 4 carbon atoms, represented by $R^a$ to $R^i$, includes those exemplified in the description of the general formula (II); a group resulting from replacement of a methylene group of the alkyl group by —O— include methoxy, ethoxy, propyloxy, isopropyloxy, methoxymethyl, ethoxymethyl, 2-methoxyethyl, and the like; a group resulting from replacement of a methylene group of the alkyl group by —CO— includes acetyl, 1-carbonylethyl, acetylmethyl, 1-carbonylpropyl, 2-oxobutyl, 2-acetylethyl, 1-carbonylisopropyl, and the like.

In the general formula (III), the alkylene group represented by Q and having 1 to 8 carbon atoms which may be substituted, includes methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethan-1,1-diyl, propan-2,2-diyl, and the like; a group resulting from replacement of a methylene group of the alkylene group by —O—, —S—, —CO—, —COO—, —OCO—, —$SO_2$—, —NH—, —CONH—, —NHCO—, —N=CH—, or —CH=CH— includes methyleneoxy, ethyleneoxy, oxymethylene, thiomethylene, carbonylmethylene, carbonyloxymethylene, methylenecarbonyloxy, sulfonylmethylene, aminomethylene, acetylamino, ethylenecarboxyamide, ethane imide-yl, ethenylene, propenylene, and the like; the metal atom represented by M includes Fe, Co, Ni, Ti, Cu, Zn, Zr, Cr, Mo, Os, Mn, Ru, Sn, Pd, Rh, Pt, Ir, and the like.

As the indolium compound of the present invention, represented by the general formula (I), those represented by the following general formula (IV) or (V) are preferable because they are easy to synthesize and are very soluble in organic solvents.

Especially, in the general formula (IV), the indolium compounds, wherein the groups represented by $R^3$ and $R^4$ are alkyl groups having 1 to 8 carbon atoms, groups which link $R^3$ and $R^4$ together to form a 5- or 6-membered heterocyclic ring without a multiple bond, or groups which link with the benzene ring to which $NR^3R^4$ is bonded to form a 5- or 6-membered ring, are preferable because their production costs are low and their molar absorption coefficients are large:

[Formula 4]

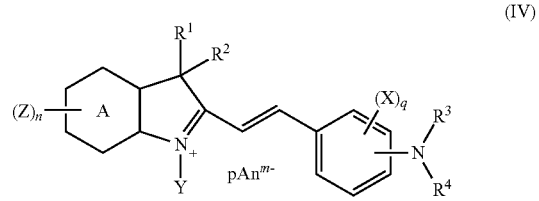

(IV)

wherein $R^3$ and $R^4$ each independently represent a hydrogen atom, an organic group having 1 to 30 carbon atoms, or a group represented by the general formula (III); $R^3$ and $R^4$ may be linked together to form a 5- or 6-membered heterocyclic ring without a multiple bond or may be linked with the benzene ring to which $NR^3R^4$ is bonded to form a 5- or 6-membered ring; X, as a substituent, represents an alkyl group having 1 to 8 carbon atoms which may contain a halogen atom or a hydroxy group or may be interrupted by an ether bond or as a substituent, an alkoxy group having 1 to 8 carbon atoms which may contain a halogen atom or a hydroxy group or may be interrupted by an ether bond, or a hydroxy, nitro, cyano, or halogen group; q represents an integer from 0 to 4; the ring A, Z, $R^1$, $R^2$, Y, $An^{m-}$, n, and p are the same as in the general formula (I).

[Formula 5]

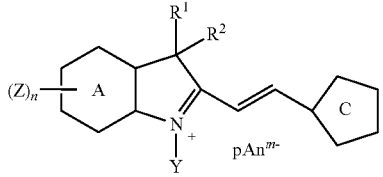

(V)

wherein the ring C represents a 5-membered heterocyclic ring; the ring A, Z, $R^1$, $R^2$, Y, $An^{m-}$, n, and p are the same as in the general formula (I).

In the general formula (IV), the organic group having 1 to 30 carbon atoms, represented by $R^3$ and $R^4$, includes those exemplified in the description of the general formula (I).

The 5- or 6-membered heterocyclic ring without a multiple bond, formed by linking of $R^3$ and $R^4$, includes a pyrrolidine, imidazolidine, pyrazolidine, thiazolidine, isothiazolidine, oxazolidine, isoxazolidine, piperidine, piperazine, and morpholine rings. In addition, the group which forms a 5- or 6-membered ring structure by linking with the benzene ring includes a hydrocarbyl group such as —$CH_2$—$CH_2$—, —$CH_2$—$CH_2$—$CH_2$—, —CH=CH—, —$CH_2$=CH—$CH_2$—, —$CH_2$—CH=$CH_2$—, and the like; a group obtained by replacing one of the methylene groups of these hydrocarbyl groups by O, S, and NH; a group obtained by replacing the methine group of these hydrocarbyl groups by N.

Further, as a substituent represented by X, the alkyl group having 1 to 8 carbon atoms, which may possess a halogen atom or a hydroxy group, or which may be interrupted by an ether bond, includes methyl, ethyl, propyl, isopropyl, butyl, sec-butyl, tert-butyl, isobutyl, amyl, isoamyl, tert-amyl, hexyl, cyclohexyl, heptyl, isoheptyl, tert-heptyl, n-octyl, isooctyl, tert-octyl, 2-ethylhexyl, chloromethyl, dichloromethyl, trichloromethyl, trifluoromethyl, pentafluoroethyl, hydroxymethyl, 2-hydroxyethyl, 2-hydroxypropyl, 4-hydroxybutyl, 2-methoxyethyl, 2-butoxyethyl, 2-(2-methoxyethoxy)ethyl, and the like. As a substituent represented by X, the alkoxy group having 1 to 8 carbon atoms, which may possess a halogen atom or a hydroxy group, or which may be interrupted by an ether bond, includes methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, chloromethyloxy, dichloromethyloxy, trichloromethyloxy, trifluoromethyloxy, pentafluoroethyloxy, 2-hydroxyethyloxy, 2-methyl-2-hydroxyethyloxy, 1-methyl-2-hydroxyethyloxy, 3-hydroxypropyloxy, 2-(2-hydroxyethoxy)ethyloxy, 2-methoxyethyloxy, 2-butoxyethyloxy, 2-methyl-2-methoxyethyloxy, 1-methyl-2-methoxyethyloxy, 3-methoxypropyloxy, 2-(2-methoxyethoxy)ethyloxy, and the like. A halogen group represented by X includes fluorine, chlorine, bromine, and iodine. In addition, q, which represents the number of groups represented by X, is preferably 0 or 1.

Among the indolium compounds represented by the general formula (IV), those represented by the following general formula (VI) are more preferable because their production costs are low and their molar absorption coefficients are large:

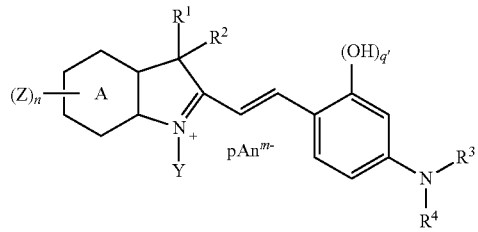

(VI)

wherein q' represents 0 or 1; the ring A, Z, $R^1$, $R^2$, Y, $An^{m-}$, n, and p are the same as in the general formula (I); $R^3$ and $R^4$ are the same as in the general formula (IV).

Among the indolium compounds represented by the general formula (V), those represented by the following general formula (VII) are more preferable because they are easy to synthesize and are very soluble in organic solvents:

[Formula 7]

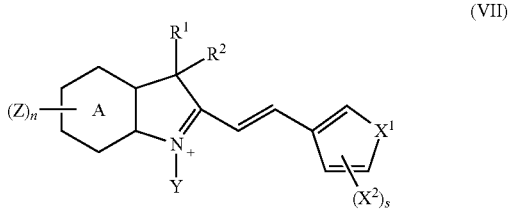

(VII)

wherein $X^1$ represents an oxygen, sulfur, or selenium atom, or —$NR^{11}$—; $X^2$ represents an alkyl group having 1 to 8 carbon atoms, an alkoxy group having 1 to 8 carbon atoms, a hydroxy, nitro, cyano, or halogen group; $R^{11}$ represents an alkyl group having 1 to 8 carbon atoms or an aryl group having 6 to 20 carbon atoms; s represents an integer from 0 to 3; the ring A, Z, $R^1$, $R^2$, Y, $An^{m-}$, n, and p are the same as in the general formula (I).

In the general formula (VII), the alkyl group having 1 to 8 carbon atoms, represented by $X^2$ and $R^{11}$, includes methyl, ethyl, propyl, isopropyl, butyl, sec-butyl, tert-butyl, isobutyl, amyl, isoamyl, tert-amyl, hexyl, cyclohexyl, cyclohexylmethyl, cyclohexylethyl, heptyl, isoheptyl, tert-heptyl, n-octyl, isooctyl, tert-octyl, 2-ethylhexyl, and the like; the alkoxy group having 1 to 8 carbon atoms, represented by $X^2$, includes methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, and the like; the halogen atom represented by $X^2$ includes those groups exemplified in the description of the general formula (I).

Further, the aryl group having 6 to 20 carbon atoms, represented by $R^{11}$, includes phenyl, naphthyl, anthracen-1-yl, phenthren-1-yl, and the like.

The preferable specific examples of the indolium compound, represented by the general formula (I) of the present invention, include the following compound Nos. 1 to 85. It is noted that the following examples show only indolium cations, omitting anions. In the indolium compound of the invention, the polymethine chain may have a resonance structure:

[Formula 11]
Compound No. 1
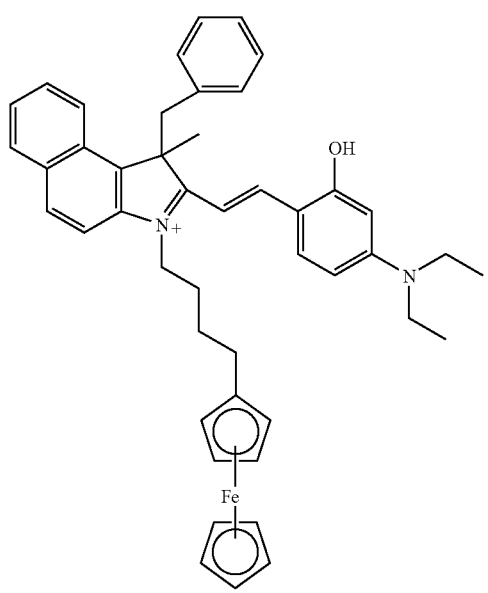
Compound No. 2
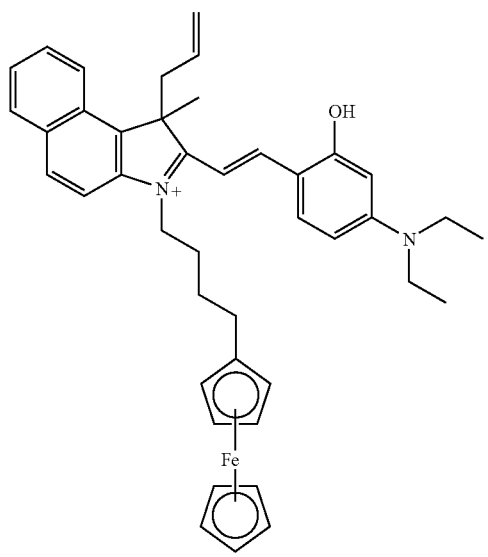
-continued
Compound No. 3
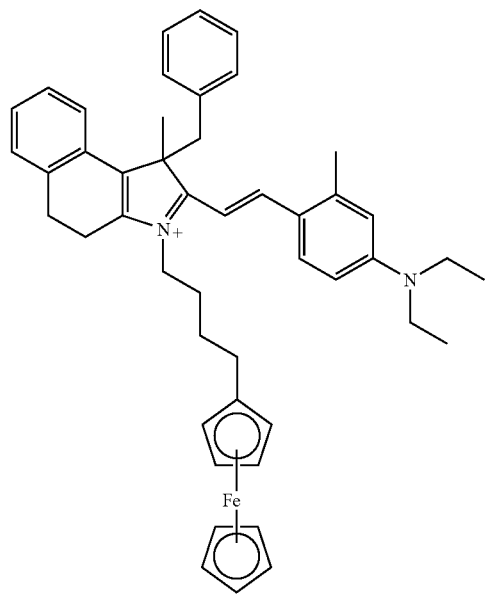
Compound No. 4
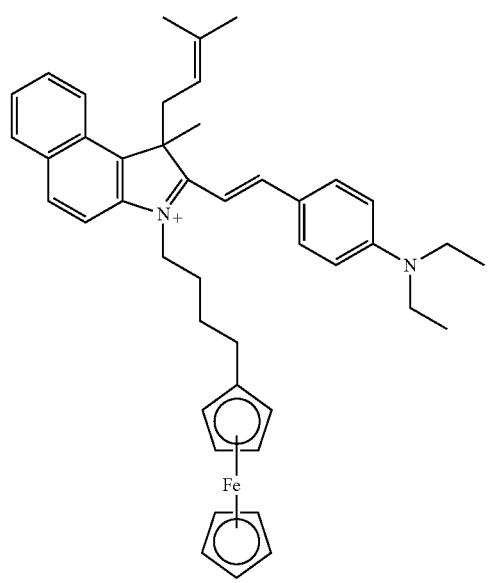

Compound No. 5
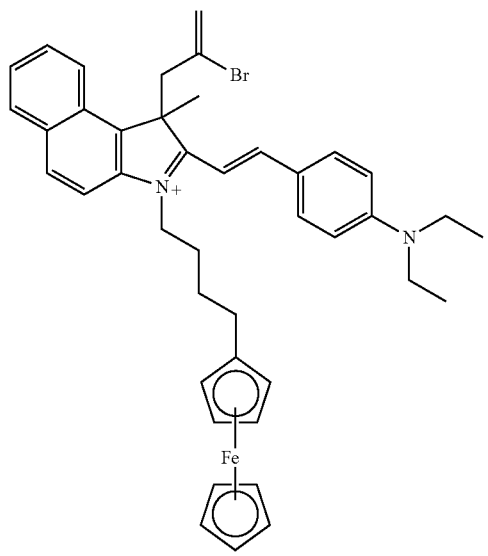
Compound No. 6
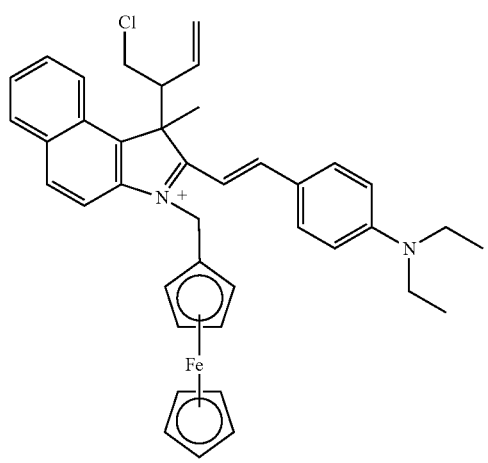
Compound No. 7
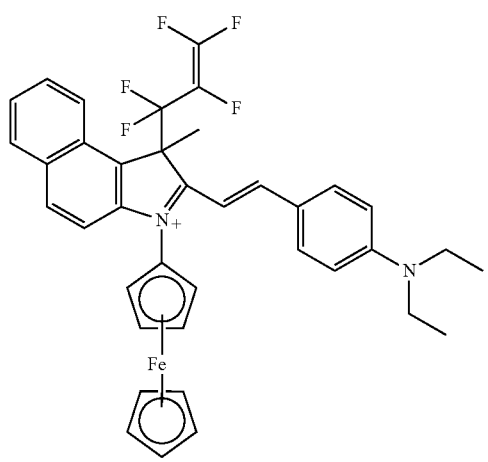
Compound No. 8
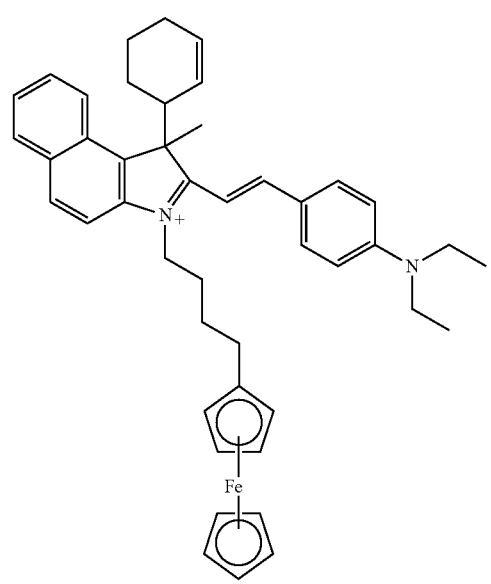
Compound No. 9
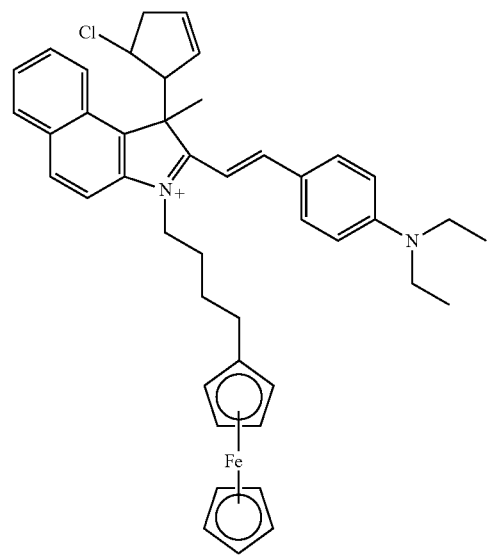

[Formula 12]
Compound No. 10
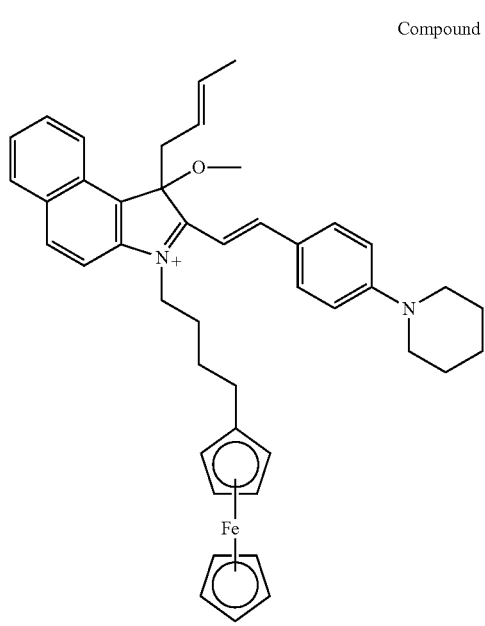
Compound No. 12
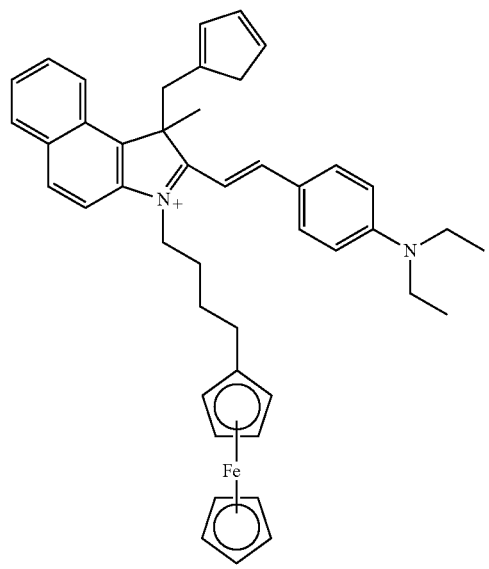
Compound No. 11
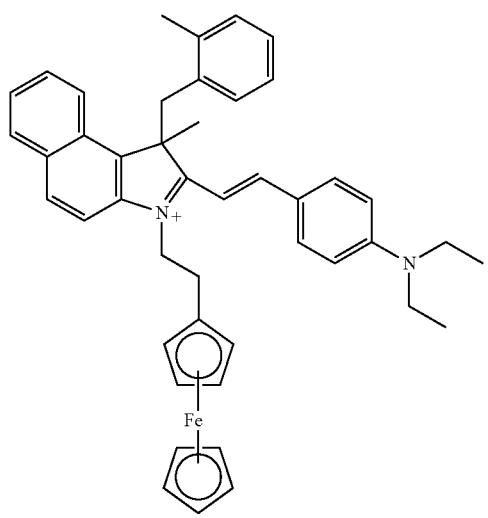
Compound No. 13
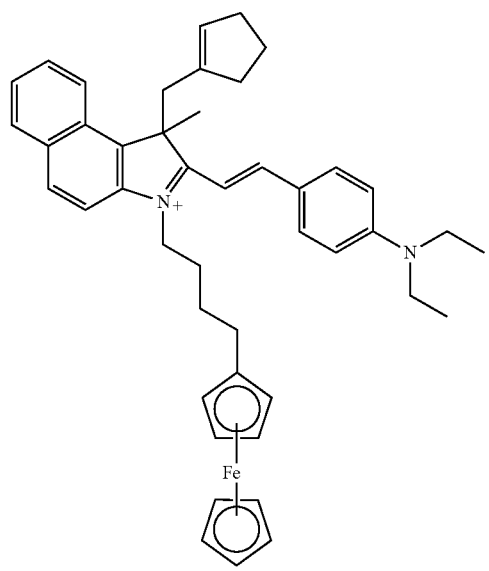

Compound No. 14
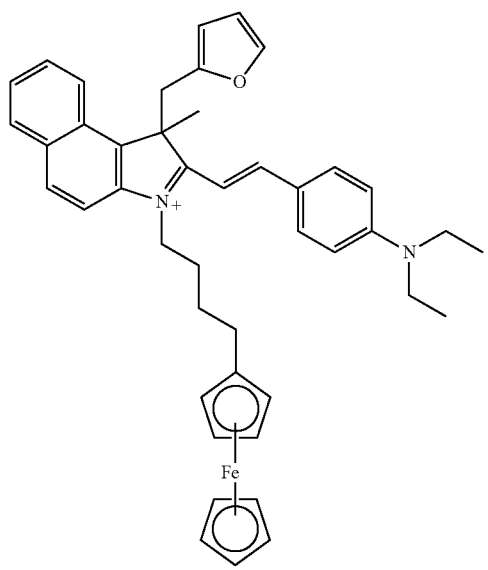
Compound No. 15
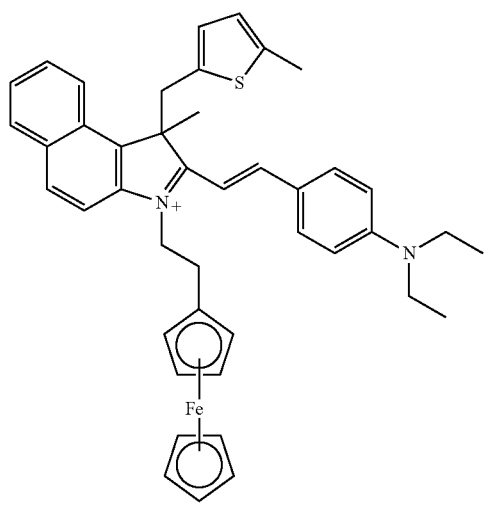
Compound No. 16
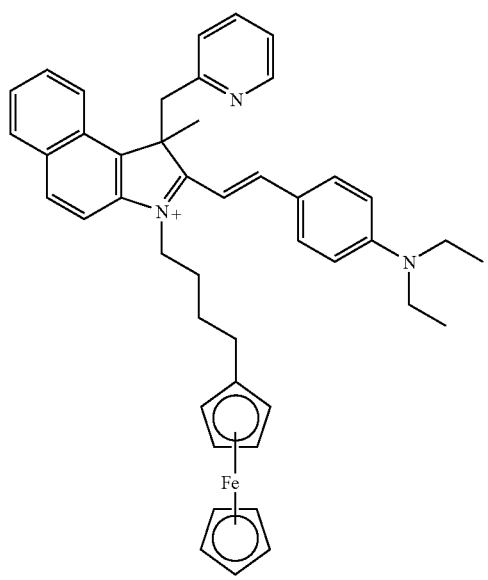
Compound No. 17
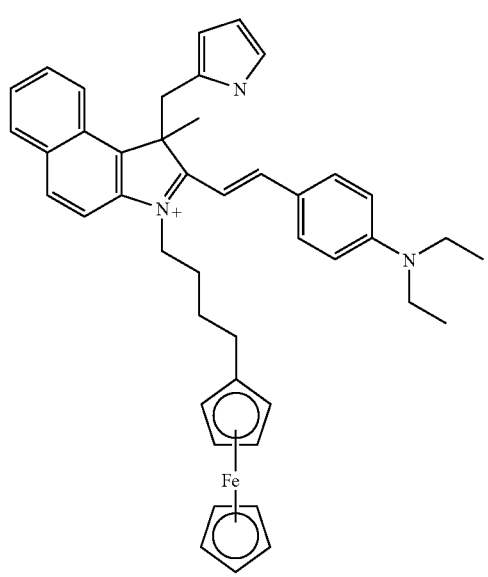
Compound No. 18
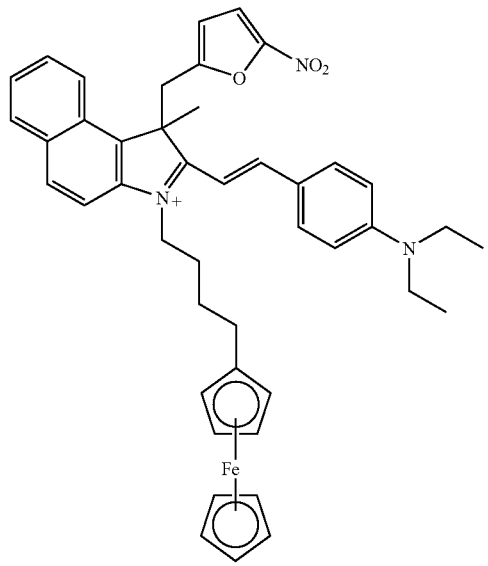

-continued
[Formula 13]
Compound No. 19
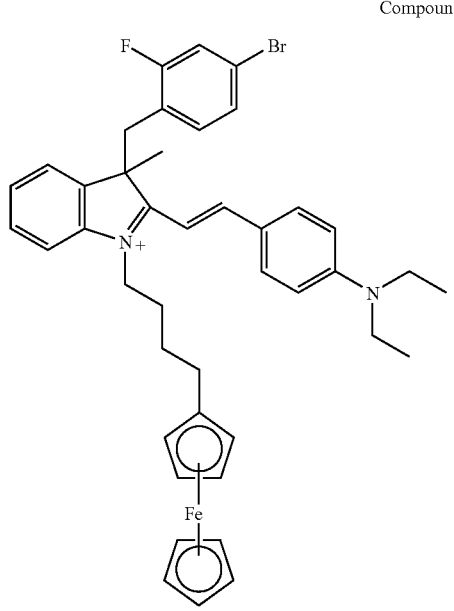
Compound No. 20
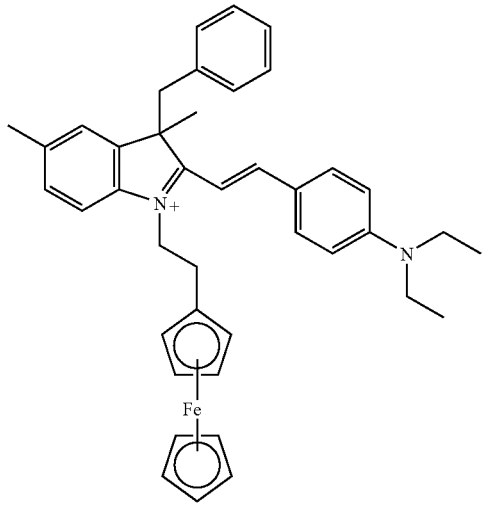
Compound No. 21
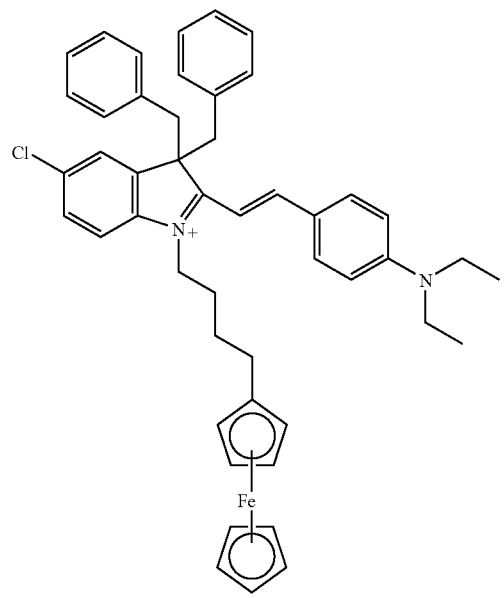
Compound No. 22
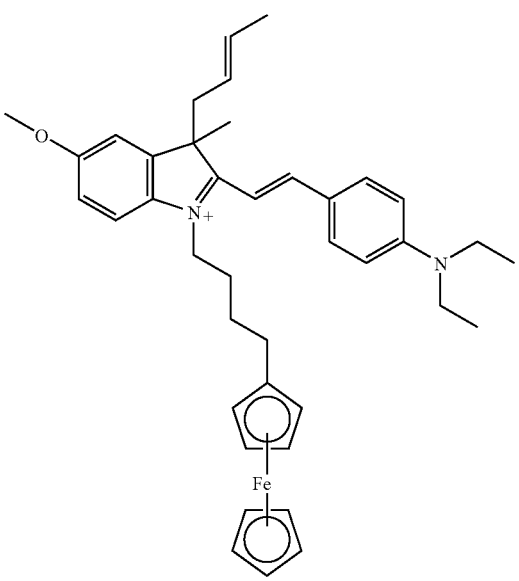

Compound No. 23
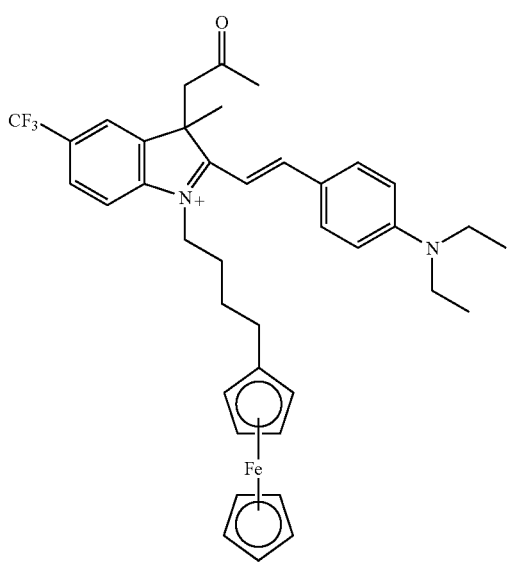
Compound No. 24
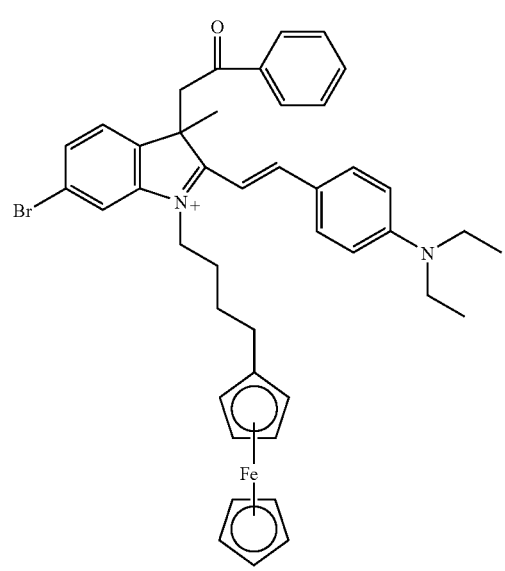
Compound No. 25
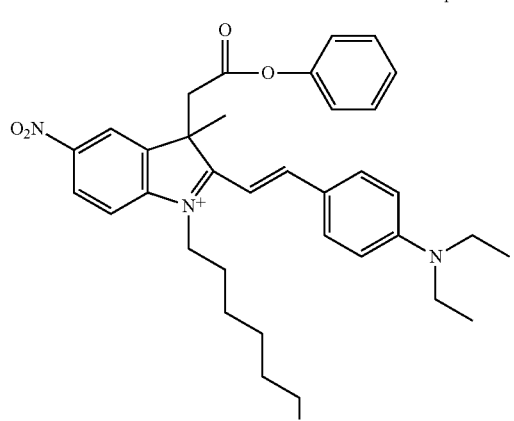
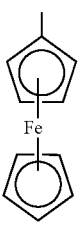
Compound No. 26
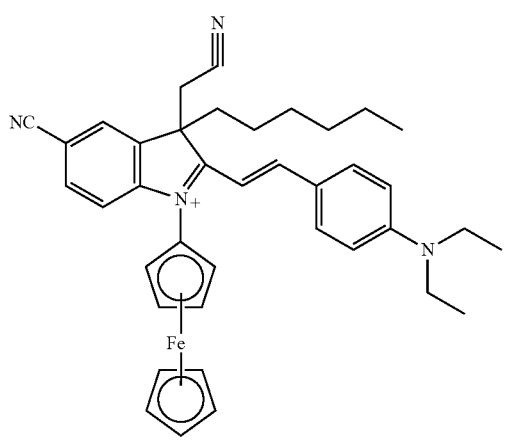
Compound No. 27
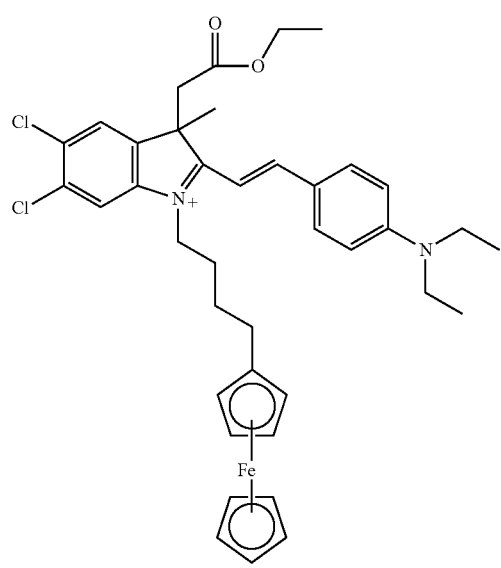

[Formula 14]
Compound No. 28
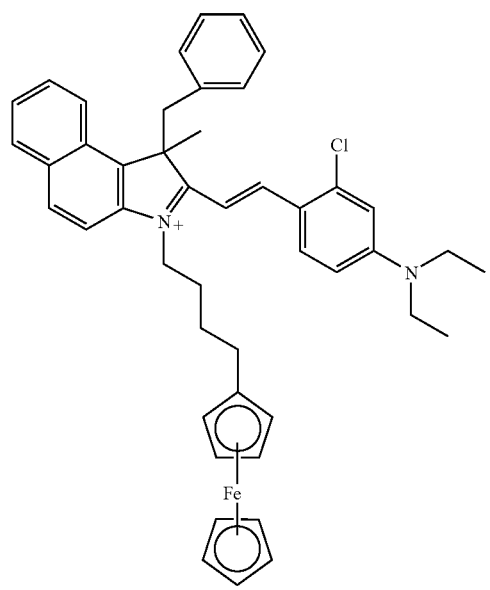
Compound No. 30
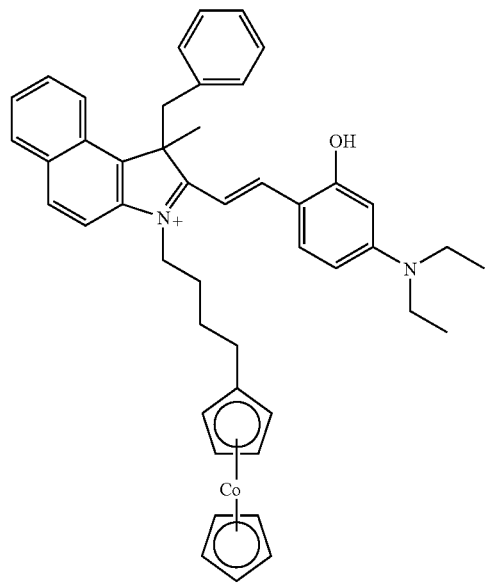
Compound No. 29
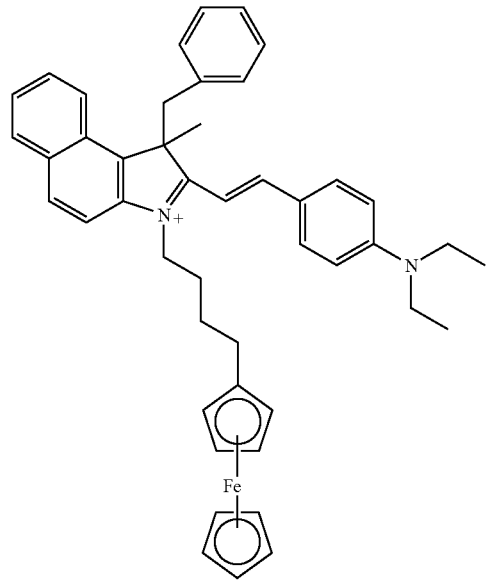
Compound No. 31
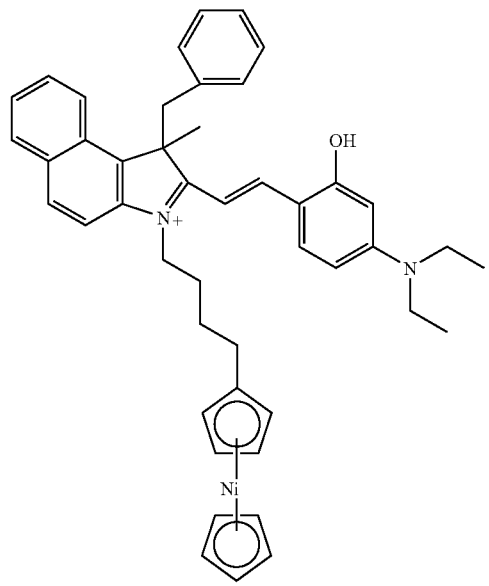

Compound No. 32
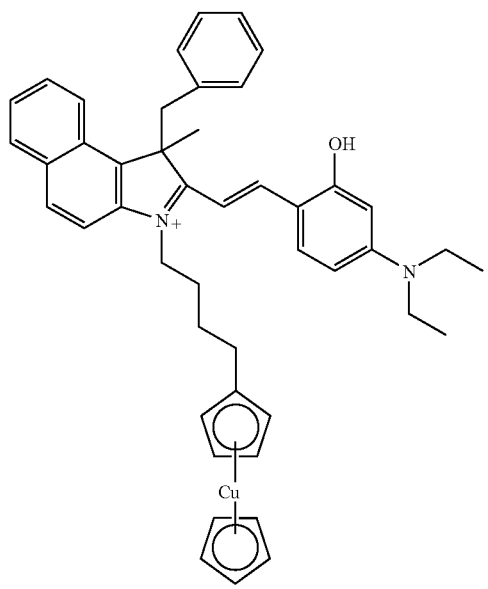
Compound No. 33
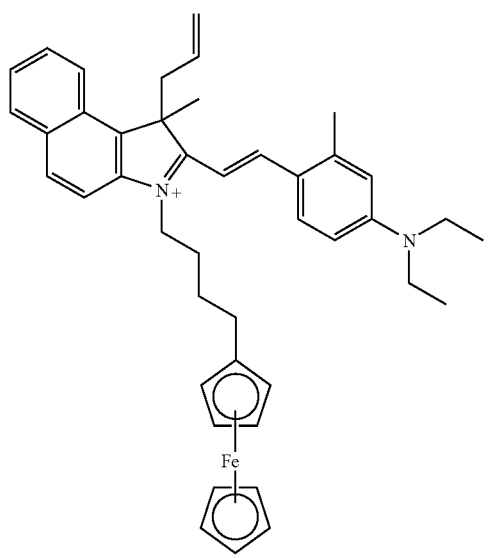
Compound No. 34
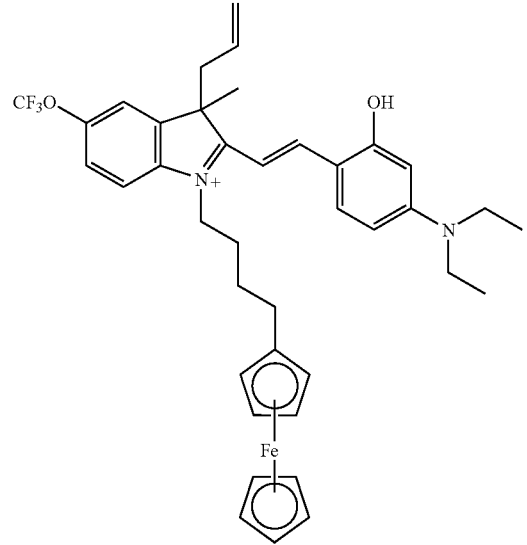
Compound No. 35
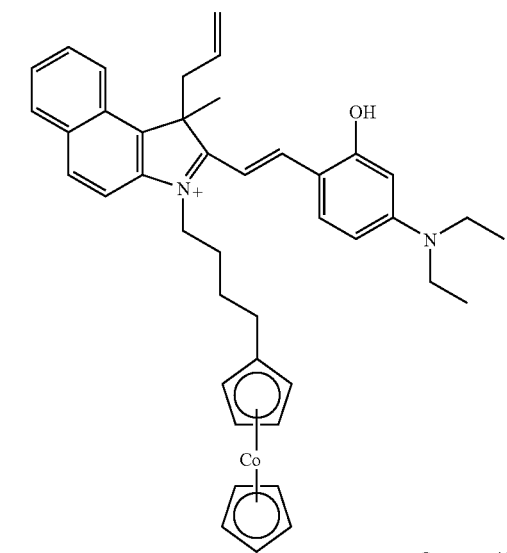
Compound No. 36
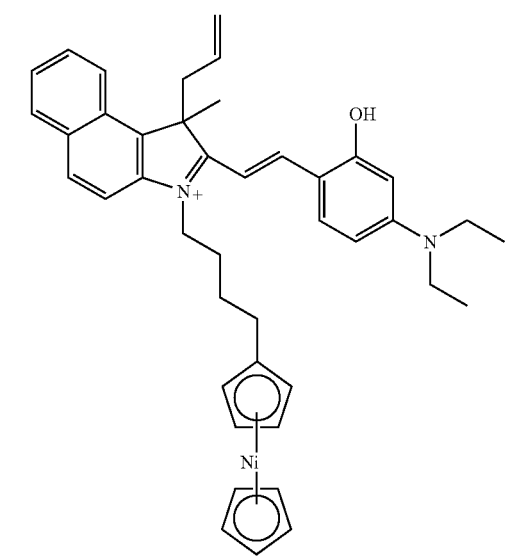

[Formula 15]
Compound No. 37
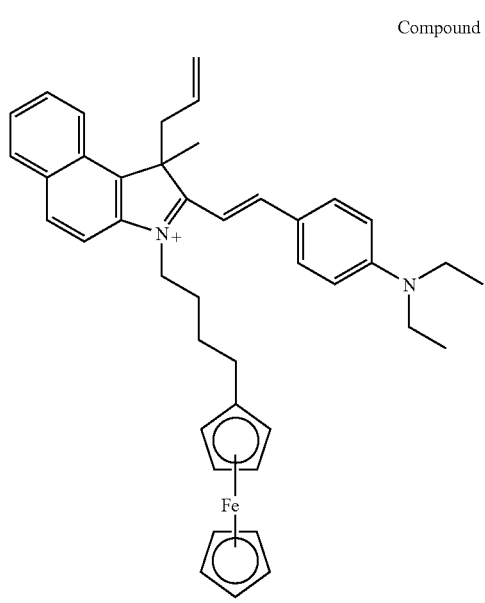
Compound No. 39
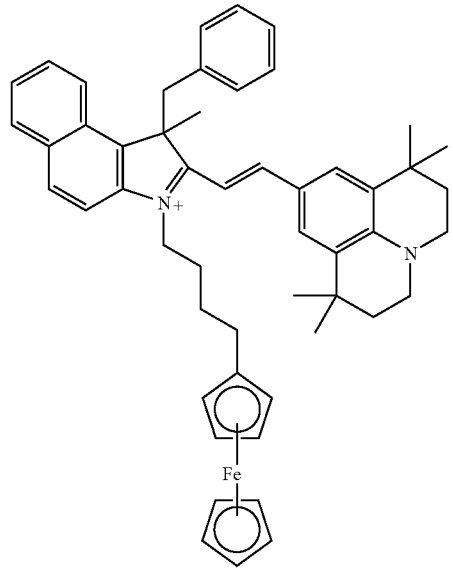
Compound No. 38
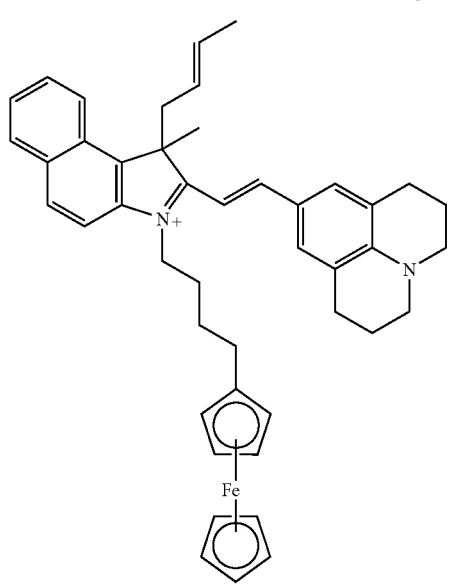
Compound No. 40
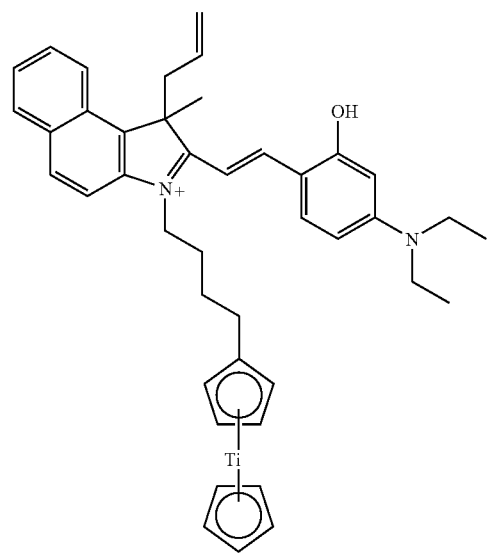

Compound No. 41
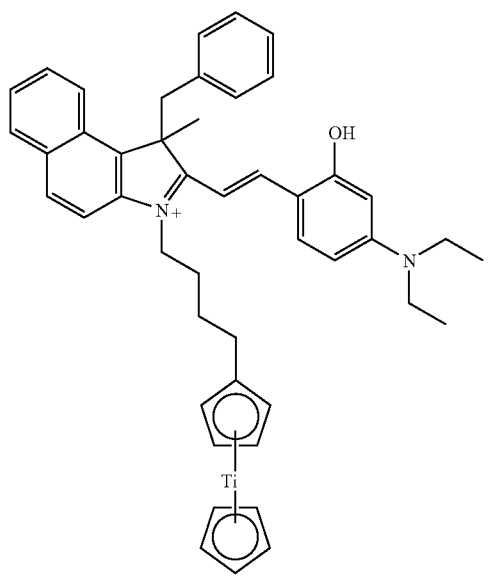
Compound No. 43
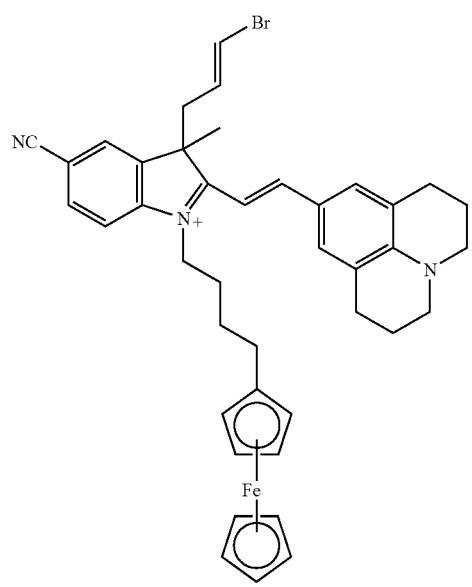
Compound No. 42
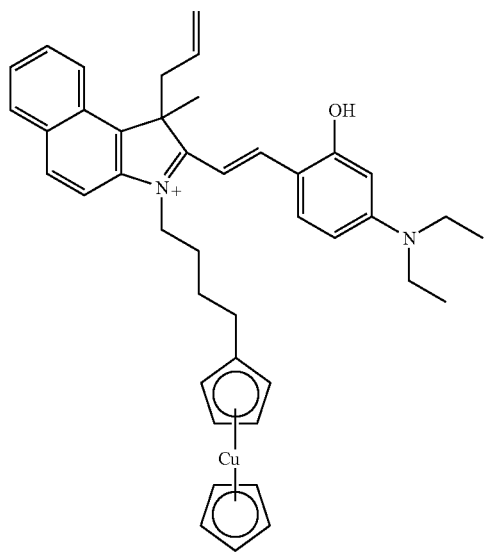
Compound No. 44

Compound No. 45
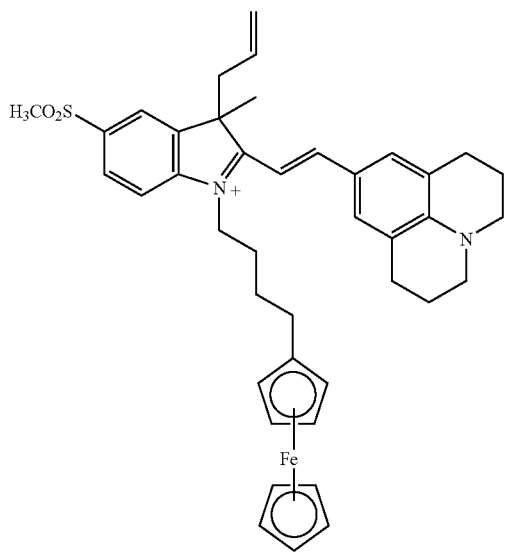
[Formula 16]
Compound No. 46
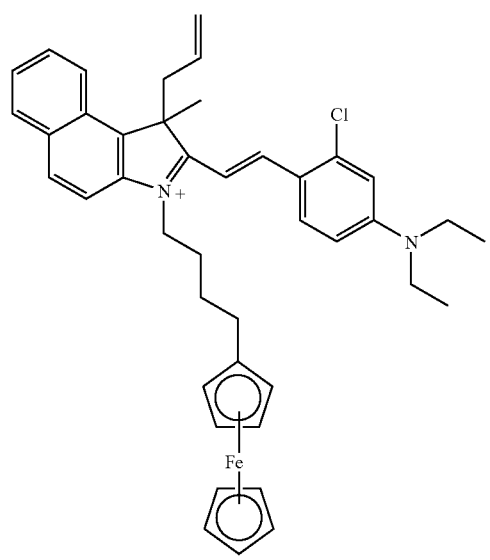
Compound No. 47
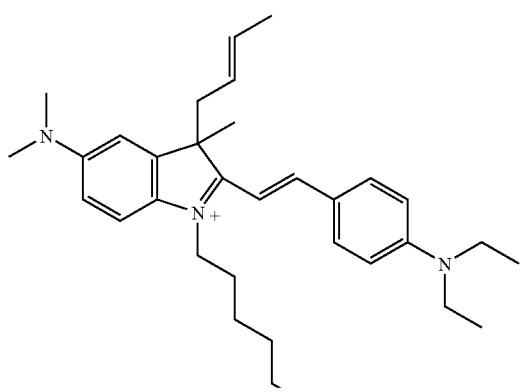
Compound No. 48
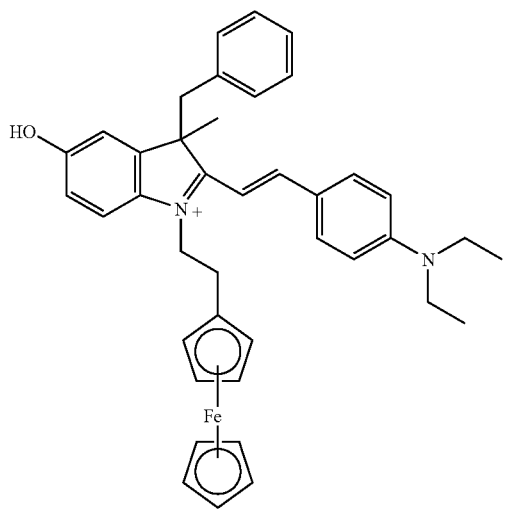
Compound No. 49
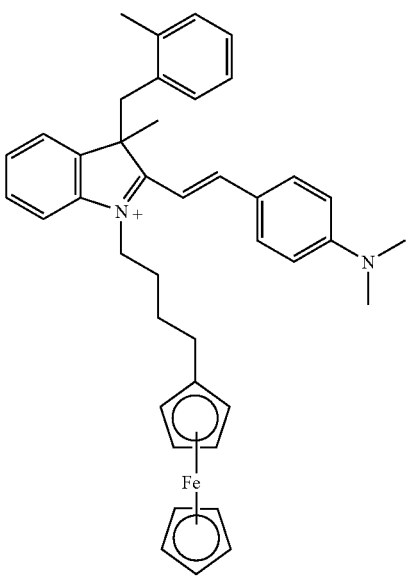

Compound No. 50
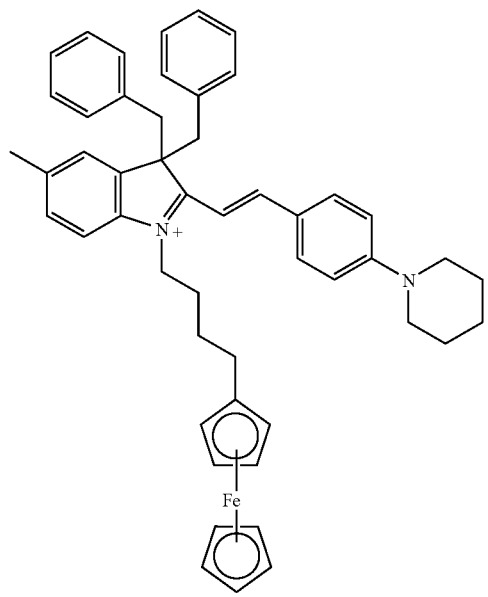
Compound No. 51
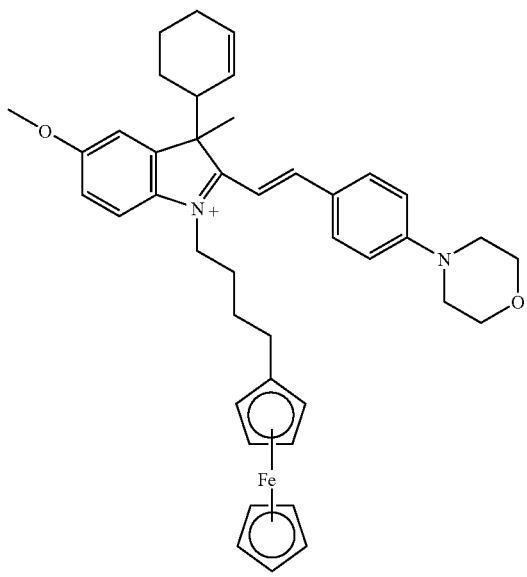
Compound No. 52
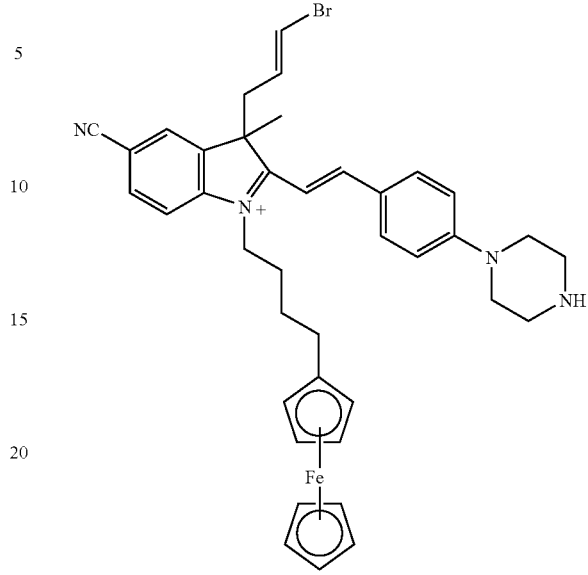
Compound No. 53
Compound No. 54
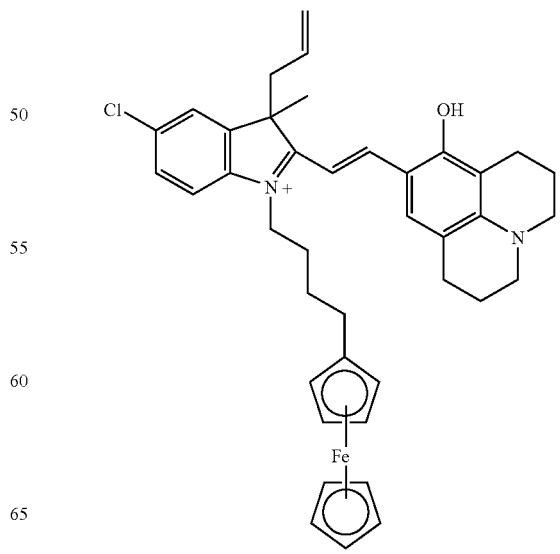

[Formula 17]
Compound No. 55
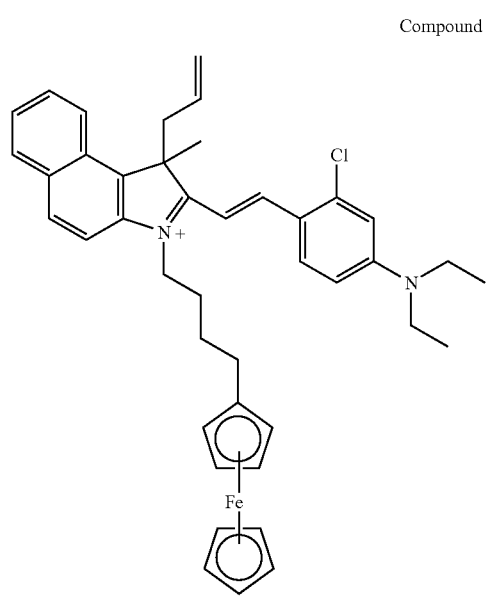
Compound No. 57
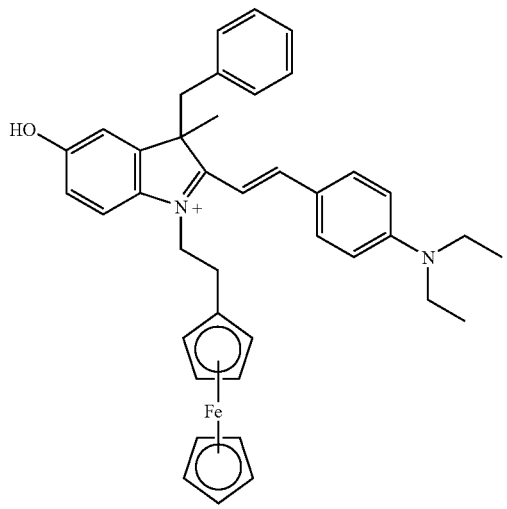
Compound No. 56
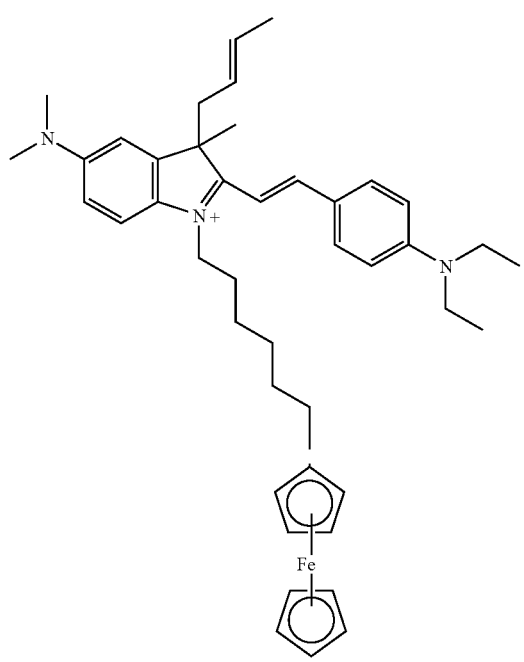
Compound No. 58
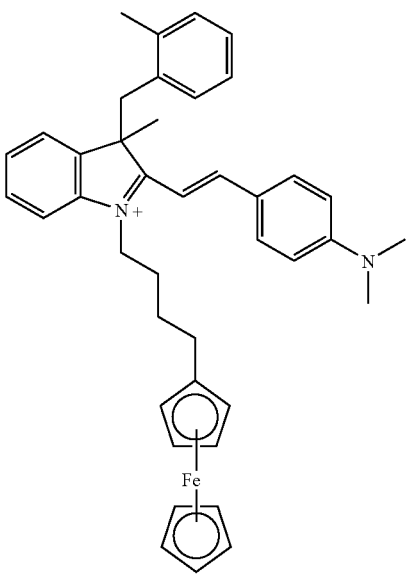

Compound No. 59
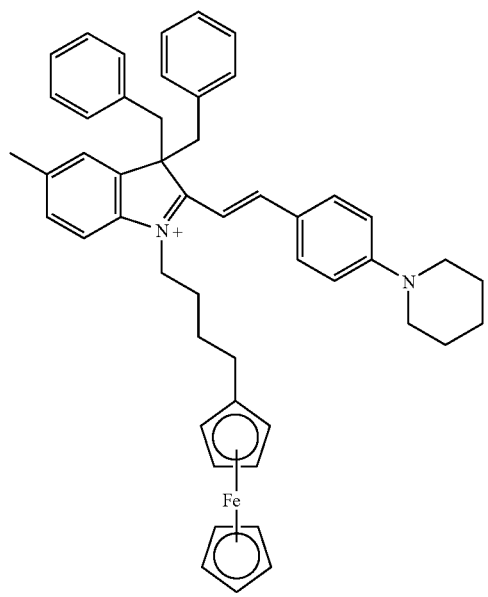
Compound No. 60
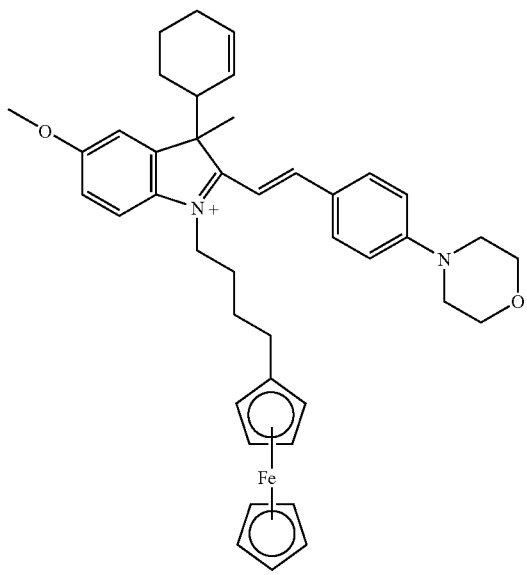
Compound No. 61
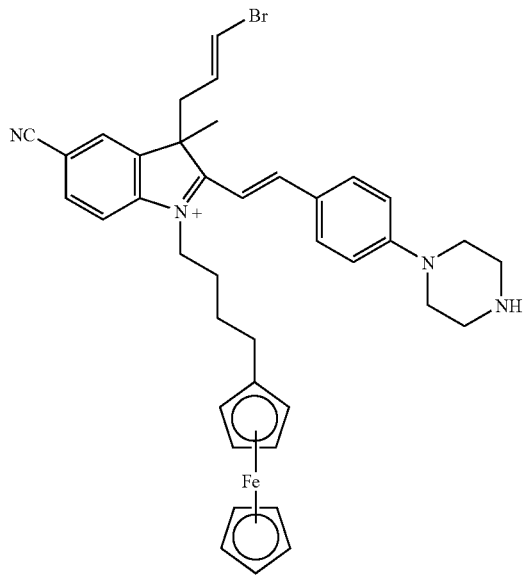
Compound No. 62
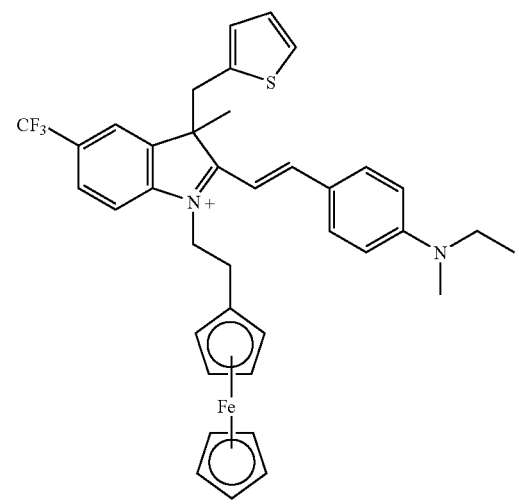
Compound No. 63
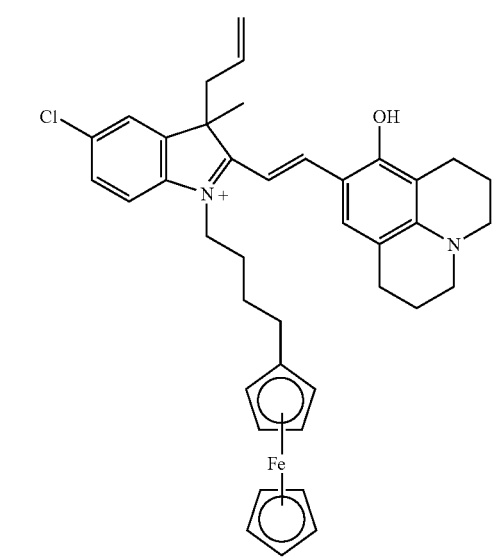

[Formula 18]
Compound No. 64
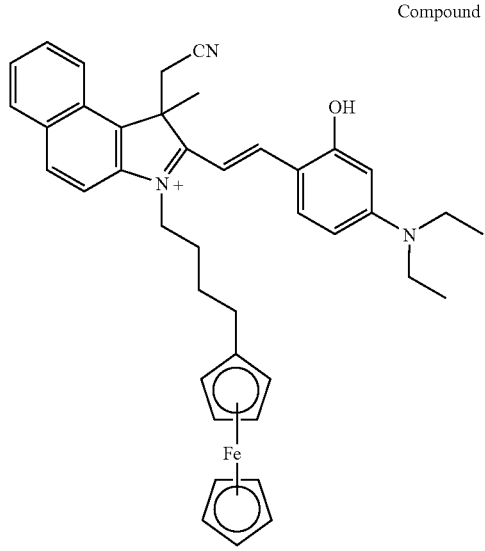
Compound No. 65
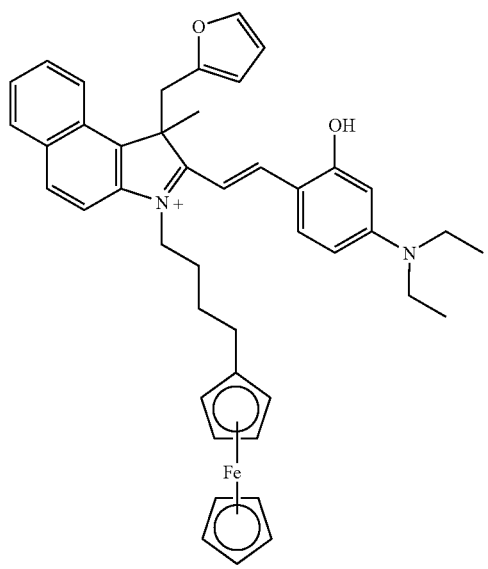
Compound No. 66
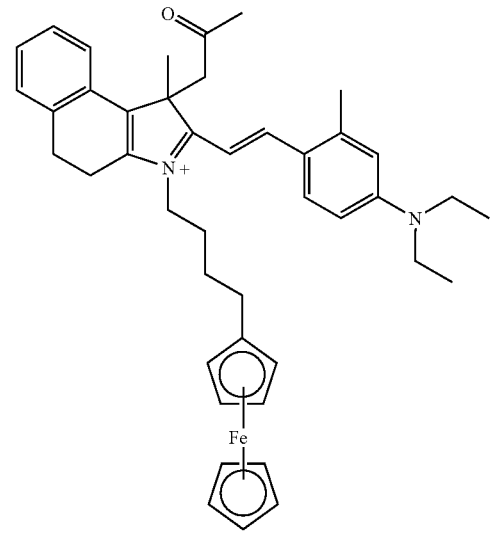
Compound No. 67
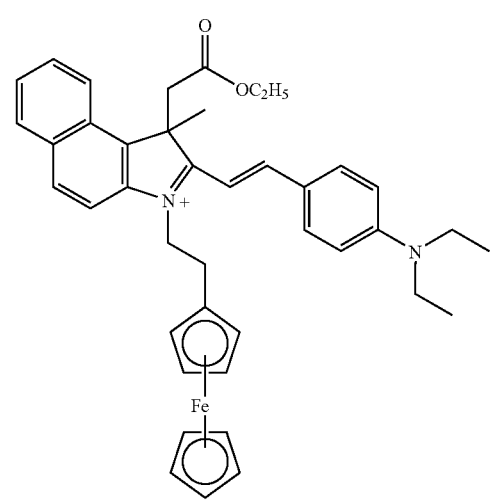
Compound No. 68

Compound No. 69
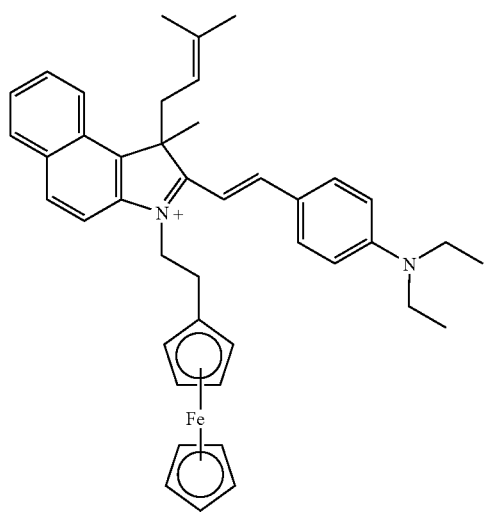
Compound No. 70
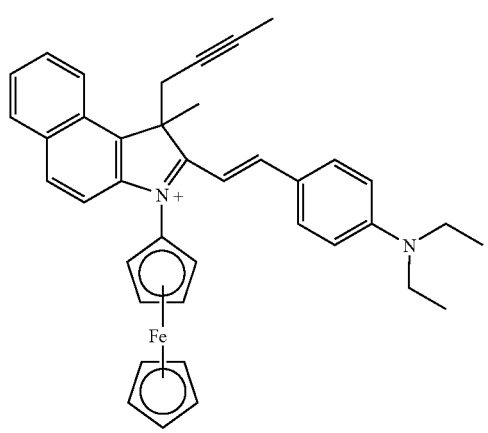
Compound No. 71
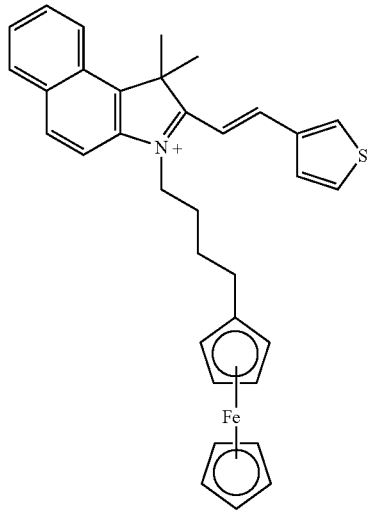
Compound No. 72
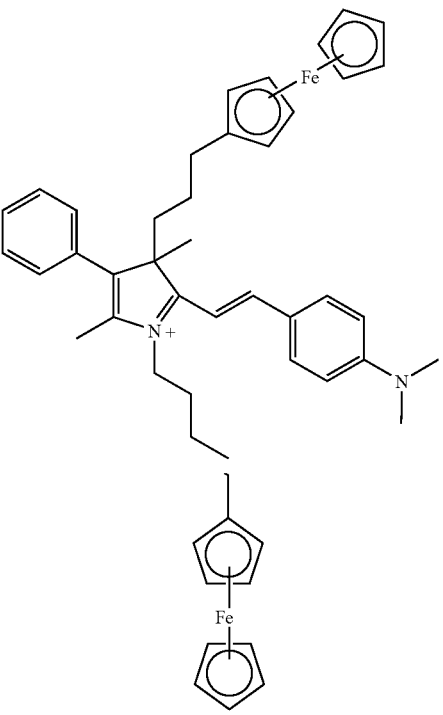
[Formula 19]
Compound No. 73
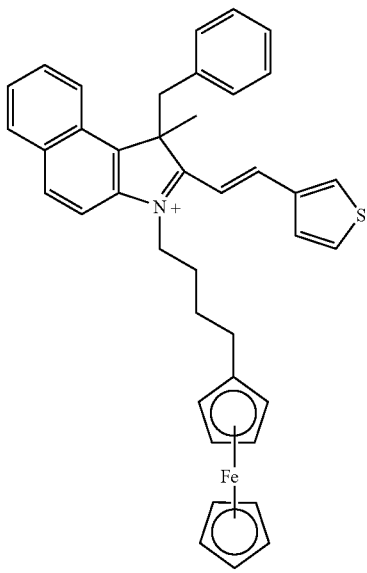

Compound No. 74
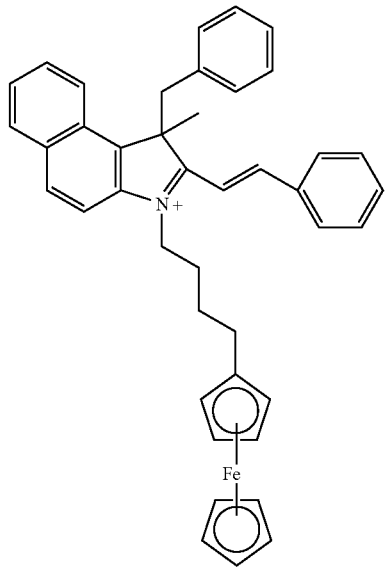
Compound No. 76
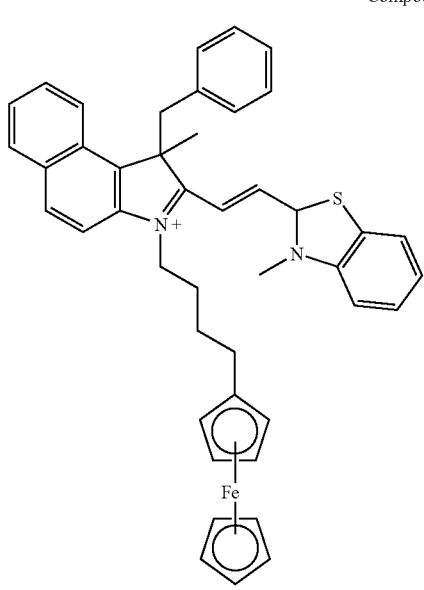
Compound No. 75
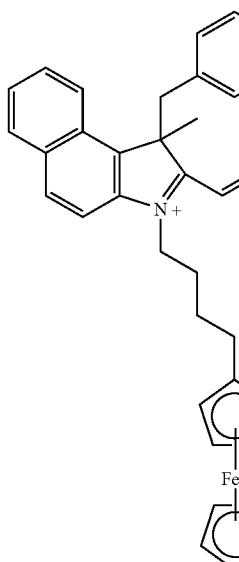
Compound No. 77

Compound No. 78
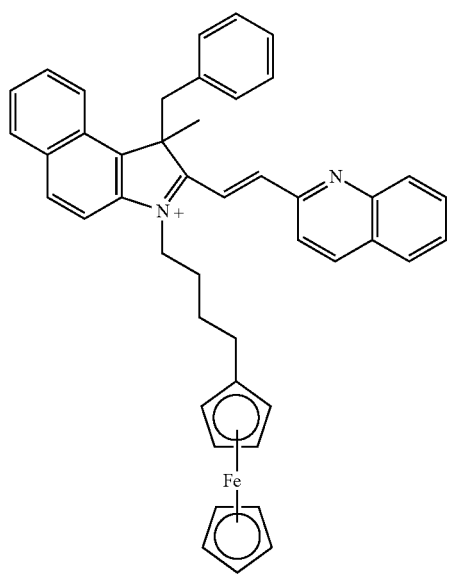
Compound No. 80
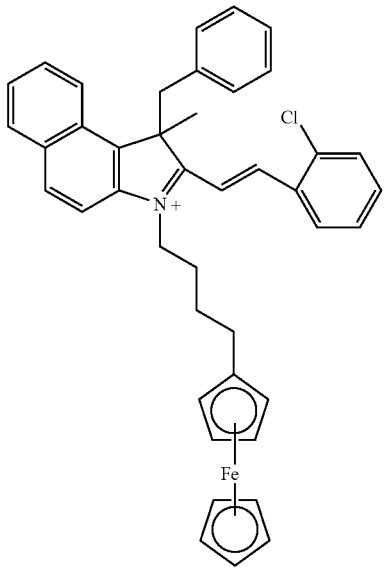
Compound No. 79
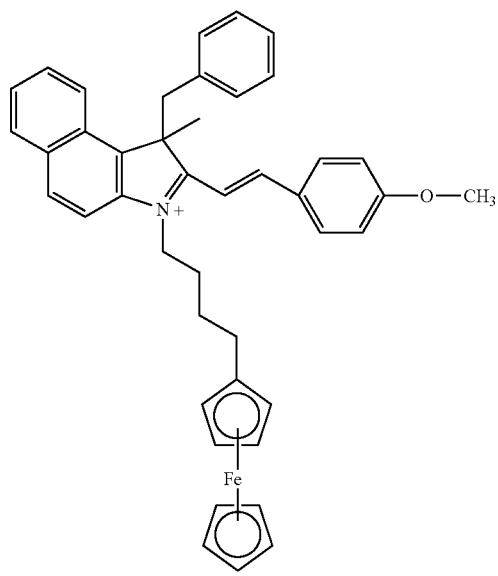
Compound No. 81
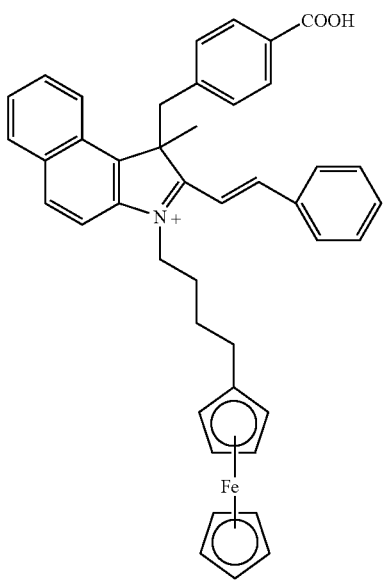

-continued

[Formula 20]

Compound No. 82

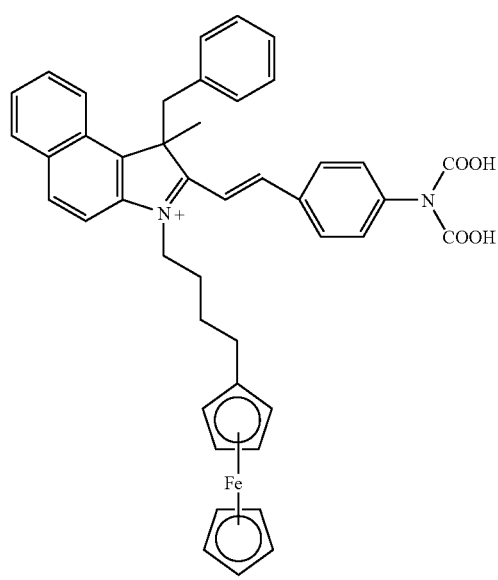

Compound No. 83

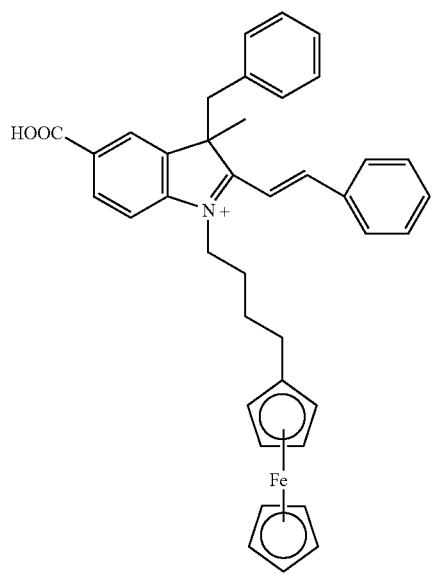

-continued

Compound No. 84

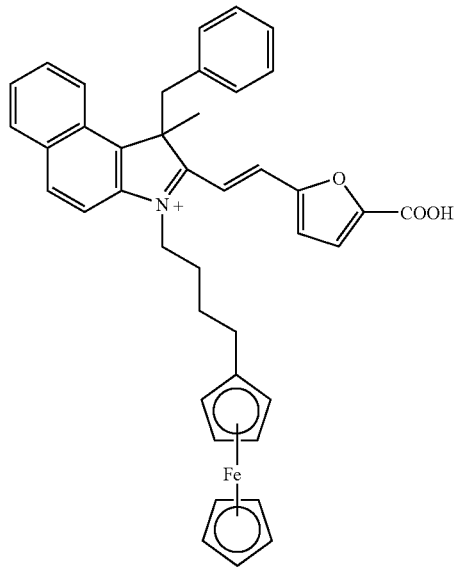

Compound No. 85

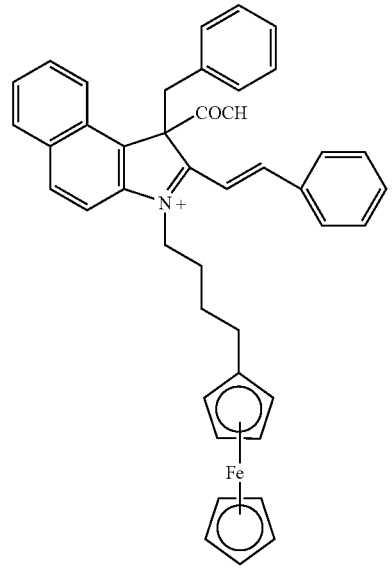

With the indolium compound of the present invention represented by the general formula (I), there are cases where optical isomers such as enantiomers, diastereomers, or a racemic mixture are present, having, as the chiral center, the chiral atom to which groups represented by $R^1$ and $R^2$ are bonded. In such a case, any optical isomer among these may be isolated and used as such or may be used as a mixture thereof.

The indolium compound of the present invention, represented by the general formula (I), is not restricted by the method of manufacture. For example, it may be synthesized by a condensation reaction of a 2-methylindole derivative and an aromatic aldehyde derivative, followed by a salt exchange reaction.

Further, the group containing a multiple bond, represented by the general formula (II), may be introduced during the process of preparing an intermediate 2-methylindole derivative. Methods for this include a method whereby a starting material, arylhydrazine derivative, is reacted with a 2-butanone derivative having the multiple bond group represented by the general formula (II) to form an indole ring, and a method whereby a halogenated derivative of the multiple bond group is reacted with an indole ring. Y may be introduced by means of Y-D which can react with NH of the indole ring, where D represents a halogen group such as chlorine, bromine, iodine, and the like; a sulfonyloxy group such as phenylsulfonyloxy, 4-methylphenylsulfonyloxy, 4-chlorophenylsulfonyloxy, and the like. Furthermore, the 2-butanone derivative containing the multiple bond group represented by the general formula (II) may be obtained by a reaction of acetone and an aldehyde having the corresponding multiple bond group.

In addition, the group containing a multiple bond, represented by the general formula (II'), may be introduced by similar methods.

The indolium compound represented by the general formula (I) is used not only as an optical recording material, but also as an optical element such as a light absorber and the like contained in an optical filter; a synthetic intermediate for pharmaceuticals, agrochemicals, perfumes, dyes, and the like, and; a raw material for various polymers such as various functional materials.

However, the present invention is not limited in any way by these applications.

Hereafter, the optical recording material and the optical recording medium of the present invention will be described.

The optical recording material of the invention contains at least one kind of indolium compound represented by the general formula (I) of the invention.

Further, the optical recording medium of the present invention is obtained by forming on a substrate an optical recording layer comprising the optical recording material.

There is no particular restriction on the method for preparing the optical recording material of the present invention and on the method for manufacturing the optical recording medium of the present invention, wherein an optical recording layer comprising the optical recording material is formed on a substrate. Generally, the indolium compound of the present invention and, if necessary, various compounds described later are dissolved in an organic solvent to prepare the optical recording material as a solution, the organic solvent including a lower alcohol such as methanol, ethanol, and the like; an ether alcohol such as methyl cellosolve, ethyl cellosolve, butyl cellosolve, butyl diglycol, and the like; a ketone such as acetone, methyl ethyl ketone, methyl isobutyl ketone, cyclohexanone, diacetone alcohol, and the like; an ester such as ethyl acetate, butyl acetate, methoxyethyl acetate, and the like; an acrylic acid ester such as ethyl acrylate, butyl acrylate, and the like; fluorinated alcohols such as 2,2,3,3-tetrafluoropropanol and the like; a hydrocarbon such as benzene, toluene, xylene, and the like; a chlorinated hydrocarbon such as methylene dichloride, dichloroethane, chloroform, and the like. The optical recording material is coated on the substrate by a wet coating method including spin coating, spraying, dipping, and the like. Methods such as vapor deposition, sputtering, and the like may also be used. When using the organic solvent, its amount used is preferably such that the content of the indolium compound becomes 0.1 to 10% by mass of the optical recording material of the present invention.

The optical recording layer is formed as a thin film and its suitable thickness is usually 0.001 to 10 μm, preferably 0.01 to 5 μm.

Further, in the optical recording material of the present invention, the content of the indolium compound of the present invention is preferably 10 to 100% by mass of the solid content contained in the optical recording material of the invention. The optical recording layer is preferably formed in a manner such that the optical recording layer contains the indolium compound of the present invention in an amount of 50 to 100% by mass. To form an optical recording layer of such a content of the indolium compound, the optical recording material of the present invention more preferably contains the indolium compound of the present invention in an amount of 50 to 100% by mass based on the solid content contained in the optical recording material of the invention.

The solid content contained in the optical recording material of the invention refers to the components left after removing the components other than the solid content, namely, the solvent and the like, from the optical recording material. The solid content in the optical recording material is preferably 0.01 to 100% by mass, more preferably 0.1 to 10% by mass.

In addition to the indolium compound of the present invention, the optical recording material of the invention may contain, according to necessity, a compound usually used for an optical recording layer such as azo compounds, phthalocyanines, oxonols, squarylium compounds, indoles, styryl compounds, porphyns, azlenium compounds, chroconiemethines, pyrilium compounds, thiopyrilium compounds, triarylmethanes, diphenylmethanes, tetrahydrocholines, indophenols, anthraquinones, naphthoquinones, xanthene compounds, thiazines, acridines, oxadines, spiropyrans, fluorenes, rhodamines, and the like; a resin such as polyethylene, polyester, polystyrene, polycarbonate, and the like; a surfactant; an antistatic agent; a lubricating agent; a fire retardant; a radical trapping agent such as a hindered amine and the like; a pit formation accelerator such as a ferrocene derivative and the like; a dispersant; an antioxidant; a crosslinking agent; a light resistance improver; and the like. Further, the optical recording material of the present invention may contain, as a quencher for the singlet oxygen and the like, an aromatic nitroso compound, an aminium compound, an iminium compound, a bisiminium compound, a transition metal chelate compound, and the like. In the optical recording material of the present invention, these various compounds are used in an amount of 0 to 50% by mass based on the solid content contained in the optical recording material of the present invention.

To the optical recording material of the present invention, a diimmonium compound may be added. Addition of the diimmonium compound more effectively prevents the decrease with time in the residual rate of absorbance, observed in the optical recording medium of the present invention. When the immonium compound is added, its content is preferably between 0 and 99% by mass, more preferably between 50 and 95% by mass, of the solid contained in the optical recording material.

There is no particular restriction on the material used as the substrate on which such an optical recording layer is formed, provided that it is essentially transparent to the writing (recording) light and reading (reproducing) light, examples including resins such as polymethyl methacrylate, polyethylene terephthalate, polycarbonate, and the like; glass and the like. Further, its shape is optionally selected corresponding to the application, from a tape, drum, belt, disc, and the like.

Further, there may be formed on the optical recording layer a reflection film by a vapor deposition or sputtering method using gold, silver, aluminum, copper, and the like. Also, a protection layer may be formed using an acrylic resin, an ultraviolet curing resin, and the like.

The optical recording material of the present invention is suitable for an optical recording medium, which is recorded and reproduced by use of a semiconductor laser, especially for publicly known single-, double-, or multi-layer discs such as CD-R, DVD±R, HD-DVD-R, BD-R, and the like, each of a high-speed recording type.

EXAMPLES

Hereafter, the present invention will be described in more detail in terms of Manufacturing Examples, Examples, and Evaluation Examples. However, the present invention will not be limited in any way by the following Examples and the like.

The following Manufacturing Example Nos. 1 to 3 show examples of manufacture of indolium compound Nos. 1 to 3, each represented by the general formula (I).

Further, the following Examples 1 to 4 show examples of preparation of optical recording materials comprising compound Nos. 1 to No. 3 each obtained in the Manufacturing Example Nos. 1 to 3 respectively. The Examples also show the manufacturing examples of the optical recording media Nos. 1 to 3 sing the optical recording materials.

The following Comparative Examples 1 and 2 show examples of preparation of the comparative optical recording materials using indolium compounds having different structures from those represented by the general formula (I) and manufacturing examples of the comparative optical recording media No. 1 and No. 2 using the comparative optical recording materials.

In the following Evaluation Examples 1-1 to 1-3 and Comparative Evaluation Examples 1-1 and 1-2, light resistance of the optical recording media Nos. 1 to 3 obtained in Examples 1 to 3 as well as the comparative optical recording media Nos. 1 and 2 obtained in the Comparative Examples 1 and 2 was evaluated by measuring the residual rate of absorbance at the maximum absorption wavelength ($\lambda$max) in the UV absorption spectrum. The data are shown in [Table 2].

Manufacturing Examples 1 to 4

Manufacture of Hexafluorophosphate Salts of Indolium Compound Nos. 1 and 3, and Perchlorate Salts of Compound Nos. 2 and 73

Using the synthetic method described below, indolium compound Nos. 1 to 3 and No. 73 were synthesized. The compounds obtained were identified by $^1$H-NMR analysis. The analytical results of compound Nos. 1 to 3 are shown in [FIG. 1] to [FIG. 3], respectively. In [Table 1] are also shown the yields of the compounds obtained and the results of measurement of the characteristic values [light absorption properties of solutions ($\lambda$max and $\epsilon$ at $\lambda$max), decomposition point].

It is noted that, in [Table 1], the decomposition point refers to the temperature in the differential thermal analysis performed at a heating rate of 10° C./min., whereat the mass of the sample begins to decrease.

(Synthetic Method) Synthesis of Indolium Compound Nos. 1 to 3 and No. 73

<Step 1> Synthesis of Aldehyde Derivative

To a reaction flask purged with nitrogen was charged 0.8 mol of dimethylformamide and to this was dropwise added under ice bath cooling 0.24 mol of phosphorous oxychloride, followed by 0.2 mol of an amine derivative. After stirring at room temperature for 2 hrs., the reaction mixture was dropwise added to 300 ml of ice-water. Further, 50% aqueous sodium hydroxide was added until the solution became basic. To this was added 40 g of toluene, and the oil layer was separated and washed with 40 g each of water 3 times. The solvent was removed by distillation to obtain the respective desired aldehyde derivative.

<Step 2> Synthesis of Ferrocenyl Indole

To a reaction flask purged with nitrogen were charged 0.04 mol of a 2-methylindole derivative, 0.044 mol of ferrocene alcohol tosyl ester, 0.002 mol of tetrabutylammonium bromide, and 35 g of tetrahydrofuran. To this was added 0.08 mol of sodium hydroxide in portions at 50° C. and the reaction mixture was stirred at 56° C. for 1 hr. This was followed by addition of 50 g of toluene and 75 g of water to separate the oil layer, which was washed twice with 50 g each of water. The solvent was removed by distillation and the residue obtained was recrystallized from a toluene/n-hexane mixture to obtain the respective desired ferrocenyl indole.

<Step 3> Synthesis of Quaternary Salt of Ferrocenyl Indolenine

To a reaction flask were added 0.025 mol of ferrocenyl indole obtained in Step 2, 0.038 mol of a halogenated substituent having a multiple bond, and 15 g of ethanol, and the mixture was stirred at 70° C. for 3.5 hrs. To this was added 20 g of water and 0.030 mol of sodium perchlorate or potassium hexafluorophosphate to carry out an anion exchange reaction. The mixture was washed with 20 g of water and the solvent was removed by distillation to obtain the respective desired quaternary salt of ferrocenyl indolenine.

<Step 4> Synthesis of Indolium Compound Nos. 1 to 3 and No. 73

To a reaction flask were charged 1.2 mmol of the quaternary salt of ferrocenyl indolenine obtained in Step 3, 1.2 mmol of the aldehyde derivative obtained in Step 1, and 4 g of methanol, and the mixture was stirred at 60° C. for 1.5 hrs. Further, 1 ml of pyridine was added and the reaction mixture was stirred at 60° C. for 4 hrs. The reaction products were purified by column chromatography to obtain the desired indolium compound Nos. 1 to 3 and No. 73, respectively.

TABLE 1

| | Indolium compound (Cation) | Indolium compound (Anion) | Yield (%) | $\lambda$max (nm) | $\epsilon$ ($\times 10^5$) | Decomposition point (° C.) |
|---|---|---|---|---|---|---|
| Manufacturing Example 1 | Compound No. 1 | $PF_6^-$ | 29 | 585.0 | 1.17 | 246.0 |
| Manufacturing Example 2 | Compound No. 2 | $ClO_4^-$ | 35 | 584.0 | 1.31 | 186.5 |
| Manufacturing Example 3 | Compound No. 3 | $PF_6^-$ | 50 | 601.5 | 1.04 | 254.1 |
| Manufacturing Example 4 | Compound No. 73 | $ClO_4^-$ | 44 | 453.0 | 0.187 | 167.0 |

Examples 1 to 3

The indolium compound Nos. 1 to 3 obtained in the Manufacturing Examples 1 to 3 were each dissolved in 2,2,3,3-tetrafluoropropanol in a concentration of 1.0% by mass to obtain the optical recording materials as solutions. The optical recording material was spin coated on a polycarbonate disc substrate of 12 cm diameter to form a 100 nm thick optical recording layer, the disc having been provided with a foundation layer (0.01 µm) by coating a titanium chelate compound (T-50: manufactured by Nippon Soda Co., Ltd.), followed by hydrolysis. Thus were obtained the respective optical recording media Nos. 1 to 3.

Comparative Examples 1 and 2

Except that the following comparative compounds No. 1 and No. 2 were used instead of the indolium compound of the present invention, the comparative optical recording material was prepared and, using the comparative optical recording material, the comparative optical recording media No. 1 and No. 2 were obtained in a similar manner as in Examples 1 to 3.

[Formula 21]

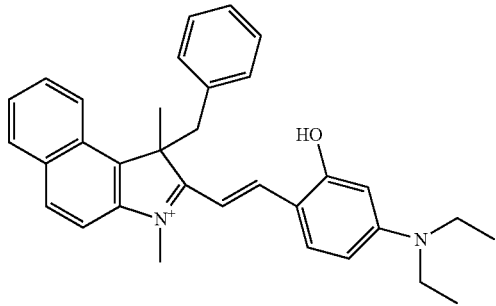

Comparative compound No. 1

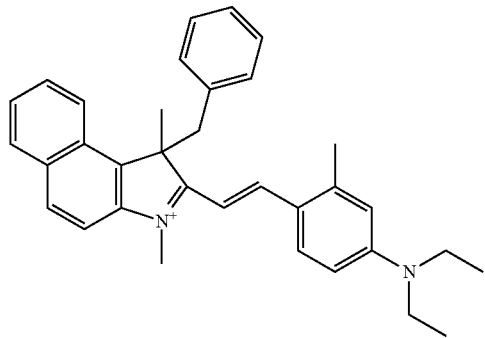

Comparative compound No. 2

Evaluation Examples 1-1 to 1-3 and Comparative Evaluation Examples 1-1 and 1-2

The light resistance was evaluated of the optical recording media No. 1 to No. 3 obtained in Examples 1 to 3 and the comparative optical recording media No. 1 and No. 2 obtained in Comparative Examples 1 and 2. As for evaluation, each of the optical recording media was irradiated by light of 55,000 lux and after 50 hrs' and 100 hrs' irradiation, the residual rate of absorbance at λmax in the UV spectrum relative to the absorbance before irradiation was measured. The results are shown in the following [Table 2].

TABLE 2

| No. | Optical recording medium | Indolium compound (Cation) | Indolium compound (Anion) | Residual rate of absorbance (%) | |
|---|---|---|---|---|---|
| | | | | After 50 hrs. | After 100 hrs. |
| Evaluation Example 1-1 | Optical recording medium No. 1 | compound No. 1 | $PF_6^-$ | 91.1 | 88.2 |
| Evaluation Example 1-2 | Optical recording medium No. 2 | compound No. 2 | $ClO_4^-$ | 90.1 | 89.5 |
| Evaluation Example 1-3 | Optical recording medium No. 3 | compound No. 3 | $PF_6^-$ | 90.5 | 88.7 |
| Comparative Evaluation Example 1-1 | Comparative optical recording medium No. 1 | Comparative compound No. 1 | $PF_6^-$ | 52.0 | 17.8 |
| Comparative Evaluation Example 1-2 | Comparative optical recording medium No. 2 | Comparative compound No. 2 | $PF_6^-$ | 6.6 | 2.2 |

As can clearly be seen from [Table 2], the optical recording media comprising optical recording layers comprised of the optical recording materials of the present invention, exhibit high residual rates of absorbance, even after 100 hrs. of light irradiation. On the other hand, the comparative recording media, comprising comparative optical recording layers comprised of the comparative optical recording materials, showed a case of lowered residual rate of absorbance after 50 hrs. of irradiation and showed a significant fall in absorbance after 100 hrs. of irradiation. Thus the light resistance of the comparative optical recording materials was not good.

INDUSTRIAL APPLICABILITY

The present invention provides a novel indolium compound and an optical recording material comprising the indolium compound, which are suitable for formation of an optical recording layer of an optical recording medium. The specific indolium compound of the present invention has a low decomposition temperature, resulting in a low heat accumulation property which suppresses the heat interference, and is also highly light resistant. Thus, the indolium compound of the invention is suitable for forming an optical recording layer of an optical recording medium.

The invention claimed is:

1. An indolium compound represented by general formula (IV):

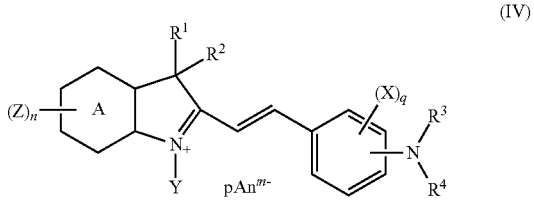

-continued

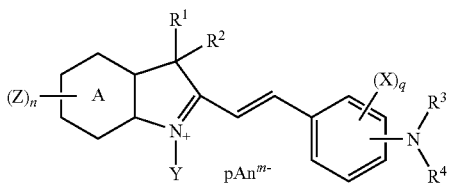
(IV)

wherein:
ring A represents a benzene or naphthalene ring;
Z represents an alkyl group having 1 to 8 carbon atoms which optionally may be substituted with a halogen atom or optionally may be interrupted by —O—, —CO—, —OCO—, or —COO—, a sulfonyl group having a hydrocarbyl group having 1 to 8 carbon atoms, a sulfinyl group having a hydrocarbyl group having 1 to 8 carbon atoms, an alkylamino group having an alkyl group having 1 to 8 carbon atoms, a dialkylamno group having alkyl groups having 1 to 8 carbon atoms, a cyano group, a nitro group, a hydroxyl group, or a halogen group;
$R^4$ represents a group represented by general formula (II) or (II');
$R^2$ represents an organic group selected from an alkyl group, an alkenyl group, an alkylaryl group and an arylalky group, or a group represented by general formula (II), (II'), or (III);
$R^3$ and $R^4$ each independently represent a hydrogen atom, an organic group selected from an alkyl group, an alkenyl group, an alkylaryl group and an arylalky group, or a group represented by general formula (III);
Y represents a group represented by general formula (III);

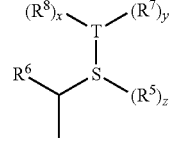
(II)

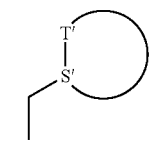
(II')

wherein, in general formula (II):
the bond between S and T is a double bond or a triple bond;
S represents a carbon atom;
T represents a carbon, oxygen, or nitrogen atom;
x, y, and z represent 0 or 1;
$R^5$ represents a hydrogen atom, a halogen atom, an alkyl group having 1 to 4 carbon atoms which optionally may be substituted with a halogen atom, or an alkoxy group having 1 to 4 carbon atoms which optionally may be substituted with a halogen atom;
$R^6$, $R^7$, and $R^8$ each independently represent a hydrogen atom, a halogen atom, an alkyl group having 1 to 4 carbon atoms which optionally may be substituted with a halogen atom; and
$R^6$ and $R^8$ may be linked together to form a ring structure,
wherein, in general formula (II'):
the bond between S' and T' is a double bond;
S' represents a carbon atom;
T' represents a carbon, oxygen, or nitrogen atom;

the ring containing S' and T' represents a 5-membered ring which optionally may contain a hetero atom or a 6-membered ring which optionally may contain a hetero atom, or a naphthalene, quinoline, isoquinoline, anthracene, or anthraquinone ring, and said rings containing S' and T' may optionally be substituted with a halogen atom, or a nitro, cyano, alkyl, or alkoxy group,

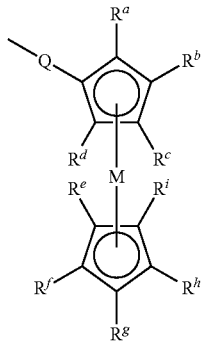
(III)

wherein, in formula (III):
$R^a$ to $R^i$ each independently represent a hydrogen atom or an alkyl group having 1 to 4 carbon atoms, where a methylene group of the alkyl group having 1 to 4 carbon atoms optionally may be replaced by —O— or —CO—;
Q represents a direct bond or an alkylene group having 1 to 8 carbon atoms which optionally may be substituted, where a methylene group of the alkylene group having 1 to 8 carbon atoms optionally may be replaced by —O—, —S—, —CO—, —COO—, —OCO—, —SO$_2$—, —NH—, —CONH—, —NHCO—, —N=CH—, or —CH=CH—; and
M represents Fe, Co, Ni, Ti, Cu, Zn, Zr, Cr, Mo, Os, Mn, Ru, Sn, Pd, Rh, Pt, or Ir;
$R^3$ and $R^4$ may be linked together to form a 5- or 6-membered heterocyclic ring without a multiple bond or may be linked with a benzene ring to which NR$^3$R$^4$ is bonded to form a 5- or 6-membered ring;
X, as a substituent, represents an alkyl group having 1 to 8 carbon atoms which optionally may contain a halogen atom or a hydroxy group or optionally may be interrupted by an ether bond or as a substituent, an alkoxy group having 1 to 8 carbon atoms which optionally may contain a halogen atom or a hydroxy group or optionally may be interrupted by an ether bond, or a hydroxy, nitro, cyano, or halogen group;
n represents an integer from 0 to 4;
q represents an integer from 0 to 4;
An$^{m-}$ represents an m-valent anion, where m is 1 or 2; and
p represents a coefficient to keep a neutral charge.

2. The indolium compound according to claim 1, said indolium compound represented by general formula (VI):

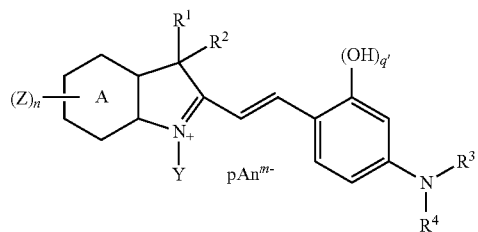
(VI)

-continued (VI)

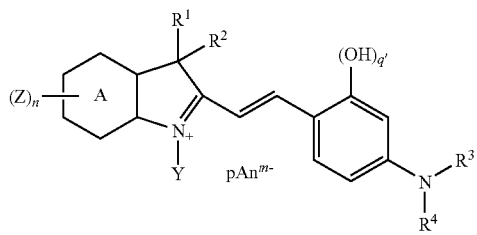

wherein q' represents 0 or 1; and
ring A, Z, $R^2$, $R^3$, $R^4$, Y, $An^{m-}$, n, and p are the same as in general formula (IV).

3. An indolium compound represented by general formula (VII):

(VII)

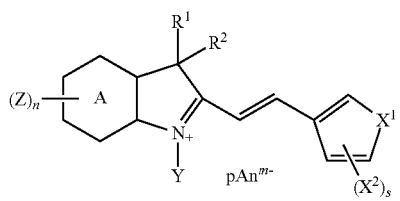

(VII)

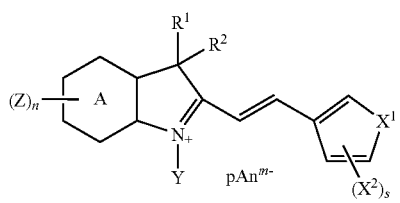

wherein:
ring A represents a benzene or naphthalene ring;
Z represents an alkyl group having 1 to 8 carbon atoms which optionally may be substituted with a halogen atom or optionally may be interrupted by —O—, —CO—, —OCO—, or —COO—, a sulfonyl group having a hydrocarbyl group having 1 to 8 carbon atoms, a sulfinyl group having a hydrocarbyl group having 1 to 8 carbon atoms, an alkylamino group having an alkyl group having 1 to 8 carbon atoms, a dialkylamno group having alkyl groups having 1 to 8 carbon atoms, a cyano group, a nitro group, a hydroxyl group, or a halogen group;
$R^1$ represents a group represented by general formula (II) or (II');
$R^2$ represents an organic group selected from an alkyl group, an alkenyl group, an alkylaryl group and an arylalky group, or a group represented by general formula (II), (II'), or (III);
Y represents a group represented by general formula (III);

(II)

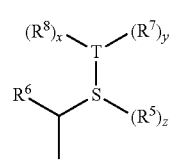

-continued (II')

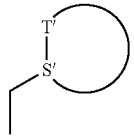

wherein, in general formula (II):
the bond between S and T is a double bond or a triple bond;
S represents a carbon atom;
T represents a carbon, oxygen, or nitrogen atom;
x, y, and z represent 0 or 1;
$R^5$ represents a hydrogen atom, a halogen atom, an alkyl group having 1 to 4 carbon atoms which optionally may be substituted with a halogen atom, or an alkoxy group having 1 to 4 carbon atoms which optionally may be substituted with a halogen atom;
$R^6$, $R^7$, and $R^8$ each independently represent a hydrogen atom, a halogen atom, an alkyl group having 1 to 4 carbon atoms which optionally may be substituted with a halogen atom; and
$R^6$ and $R^8$ may be linked together to form a ring structure,
wherein, in general formula (II'):
the bond between S' and T' is a double bond;
S' represents a carbon atom;
T' represents a carbon, oxygen, or nitrogen atom;
the ring containing S' and T' represents a 5-membered ring which optionally may contain a hetero atom or a 6-membered ring which optionally may contain a hetero atom, or a naphthalene, quinoline, isoquinoline, anthracene, or anthraquinone ring, and said rings containing S' and T' may optionally be substituted with a halogen atom, or a nitro, cyano, alkyl, or alkoxy group, (III)

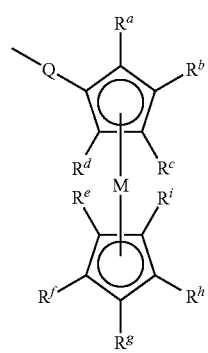

wherein, in formula (III):
$R^a$ to $R^i$ each independently represent a hydrogen atom or an alkyl group having 1 to 4 carbon atoms, where a methylene group of the alkyl group having 1 to 4 carbon atoms optionally may be replaced by —O— or —CO—;
Q represents a direct bond or an alkylene group having 1 to 8 carbon atoms which optionally may be substituted, where a methylene group of the alkylene group having 1 to 8 carbon atoms optionally may be replaced by —O—, —S—, —CO—, —COO—, —OCO—, —SO$_2$—, —NH—, —CONH—, —NHCO—, —N=CH—, or —CH=CH—; and
M represents Fe, Co, Ni, Ti, Cu, Zn, Zr, Cr, Mo, Os, Mn, Ru, Sn, Pd, Rh, Pt, or Ir;
$X^1$ represents an oxygen, sulfur, or selenium atom, or —$NR^{11}$—;

$X^2$ represents an alkyl group having 1 to 8 carbon atoms, an alkoxy group having 1 to 8 carbon atoms, a hydroxy, nitro, cyano, or halogen group; $R^{11}$ represents an alkyl group having 1 to 8 carbon atoms or an aryl group having 6 to 20 carbon atoms;

n represents an integer from 0 to 4;

s represents an integer from 0 to 3;

$An^{m-}$ represents an m-valent anion, where m is 1 or 2; and p represents a coefficient to keep a neutral charge.

4. The indolium compound according to claim 1, wherein, in the general formula (IV), the groups represented by $R^3$ and $R^4$ are:

alkyl groups having 1 to 8 carbon atoms, groups which may link $R^3$ and $R^4$ together to form a 5- or 6-membered heterocyclic ring without a multiple bond, or groups which may link with a benzene ring to which $NR^3R^4$ is bonded to form a 5- or 6-membered ring.

5. An optical recording material, comprising at least one kind of indolium compound according to claim 1, which is used for formation of an optical recording layer of an optical recording medium, the optical recording layer being disposed on a substrate.

6. An optical recording medium, comprising an optical recording layer disposed on a substrate, the layer being comprised of an optical recording material according to claim 5.

7. The indolium compound according to claim 2, wherein, in the general formula (IV), the groups represented by $R^3$ and $R^4$ are:

alkyl groups having 1 to 8 carbon atoms, groups which may link $R^3$ and $R^4$ together to form a 5- or 6-membered heterocyclic ring without a multiple bond, or groups which may link with a benzene ring to which $NR^3R^4$ is bonded to form a 5- or 6-membered ring.

8. An optical recording material, comprising at least one kind of indolium compound according to claim 2, which is used for formation of an optical recording layer of an optical recording medium, the optical recording layer being disposed on a substrate.

9. An optical recording medium, comprising an optical recording layer disposed on a substrate, the layer being comprised of an optical recording material according to claim 8.

10. An optical recording material, comprising at least one kind of indolium compound according to claim 3, which is used for formation of an optical recording layer of an optical recording medium, the optical recording layer being disposed on a substrate.

11. An optical recording medium, comprising an optical recording layer disposed on a substrate, the layer being comprised of an optical recording material according to claim 10.

* * * * *